(12) United States Patent
Chofflon et al.

(10) Patent No.: US 11,446,252 B2
(45) Date of Patent: *Sep. 20, 2022

(54) PHARMACEUTICAL COMPOSITION, COMPRISING PHOSPHATE BINDER PARTICLES

(71) Applicant: VIFOR FRESENIUS MEDICAL CARE RENAL PHARMA LTD., St. Galen (CH)

(72) Inventors: Laurent Chofflon, Zürich (CH); Erik Philipp, Arbon (CH)

(73) Assignee: Vifor Fresenius Medical Care Renal Pharma Ltd., St. Gallen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/644,612

(22) Filed: Dec. 16, 2021

(65) Prior Publication Data

US 2022/0110875 A1    Apr. 14, 2022

Related U.S. Application Data

(63) Continuation of application No. 16/820,190, filed on Mar. 16, 2020, now Pat. No. 11,234,938, which is a continuation of application No. 15/039,633, filed as application No. PCT/EP2014/075640 on Nov. 26, 2014, now Pat. No. 10,624,855.

(30) Foreign Application Priority Data

Nov. 27, 2013  (EP) .................................... 13194632
Feb. 26, 2014  (EP) .................................... 14156793

(51) Int. Cl.
| | | |
|---|---|---|
| A61K 9/20 | (2006.01) | |
| A61K 9/00 | (2006.01) | |
| A61K 33/26 | (2006.01) | |
| A61K 9/14 | (2006.01) | |

(52) U.S. Cl.
CPC .......... *A61K 9/2009* (2013.01); *A61K 9/0056* (2013.01); *A61K 9/14* (2013.01); *A61K 9/2018* (2013.01); *A61K 9/2059* (2013.01); *A61K 9/2072* (2013.01); *A61K 9/2095* (2013.01); *A61K 33/26* (2013.01)

(58) Field of Classification Search
CPC ...... A61K 9/14; A61K 9/0056; A61K 9/2095; A61K 9/2072; A61K 9/2009; A61K 9/2018; A61K 9/2059; A61K 33/26; A61P 3/00; A61P 13/12
See application file for complete search history.

(56) References Cited

U.S. PATENT DOCUMENTS

| | | |
|---|---|---|
| 5,514,281 A | 5/1996 | Boos et al. |
| 6,117,451 A | 9/2000 | Kumar |
| 6,174,442 B1 | 1/2001 | Geisser et al. |
| 2002/0044969 A1 | 4/2002 | Harden et al. |
| 2008/0014541 A1 | 6/2008 | Ambuhl et al. |
| 2008/0145410 A1* | 6/2008 | Ambuhl .................... A61P 9/00 264/109 |
| 2009/0317459 A1 | 12/2009 | Pennel et al. |
| 2010/0247609 A1* | 9/2010 | Weibel ................. A61K 9/2095 424/443 |
| 2012/0201864 A1* | 8/2012 | Applewhite .............. A61P 7/00 424/647 |

FOREIGN PATENT DOCUMENTS

| | | |
|---|---|---|
| GB | 1249558 | 10/1971 |
| WO | WO02/13793 | 2/2002 |
| WO | WO 2009/062993 | 5/2009 |
| WO | WO 2010/015827 | 2/2010 |

OTHER PUBLICATIONS

Kornblum, "Sustained-Action Tablets Prepared by Employing a Spray-Drying Technique for Granulation," Journal of Pharmaceutical Science, 1969, 58(1): 125-127.
Lanz et al., "Chewability testing in the development of a chewable tablet for hyperphosphatemia," Drug Dev Ind Pharm. Dec. 2014;40(12):1623-1631.
McCormick, "Evolutions in Direct Compression," Pharmaceutical Technology, Apr. 2005, pp. 52-62.
Mendes et al., "Chewable Tablets" in Pharmaceutical Dosage Forms: Tablets, Marcel Dekker, Inc., 1989, 2nd Edition, edited by H.A. Lieberman, L. Lachman, and J.B. Schwartz, pp. 367-417.
Mohan, "Compression physics of pharmaceutical Powders: A review," IJPSR, 2012, vol. 3(6): 1580-1592.
Pharmaceutics: The Science of Dosage Form Design, Churchill Livingstone, 2002, 2nd Edition, edited by M. E. Aulton, pp. 389, 390 & 412 (ISBN O 443 05517 5).
Remington: Pharmaceutical Sciences, Mack Printing Co., 16th edition, 1980, pp. 1553-1576.
Remington: The Science and Practice of Pharmacy, Mack Printing Co., 19th edition, vol. 11, 1995, pp. 1616-1620 and 1627-1628.
Shangraw, "Compressed Tablets by Direct Compression," in 1 Pharmaceutical Dosage Forms: Tablets, vol. 1, 195 (Herbert A. Lieberman et al., 2d ed. 1989), pp. 195-246.
Third Party Observation, filed Feb. 7, 2018 in counterpart European Appln No. 1403118.0.
Tousey, Michael D., "Optimal Tablet Press Operation Machine versus Granulation," Pharmaceutical Technology, Jan. 2002, pp. 52-60.
Yajima et al., "Optimization of Size Distribution of Granules for Tablet Compression," Chem. Pharm. Bull., 1996, 44(5), pp. 1056-1060.

\* cited by examiner

*Primary Examiner* — Doan T Phan
(74) *Attorney, Agent, or Firm* — Finnegan, Henderson, Farabow, Garrett & Dunner LLP

(57) ABSTRACT

The present invention relates to pharmaceutical composition, comprising certain phosphate binder particles having a certain particle size distribution, a process for the manufacture of the pharmaceutical composition and the use of sucroferric oxyhydroxide having a certain particle size distribution for the manufacture of a pharmaceutical composition.

16 Claims, 3 Drawing Sheets

Figure 1  Flow Chart of the Manufacturing Process for sucroferric oxyhydroxide Drug Substance (DS)
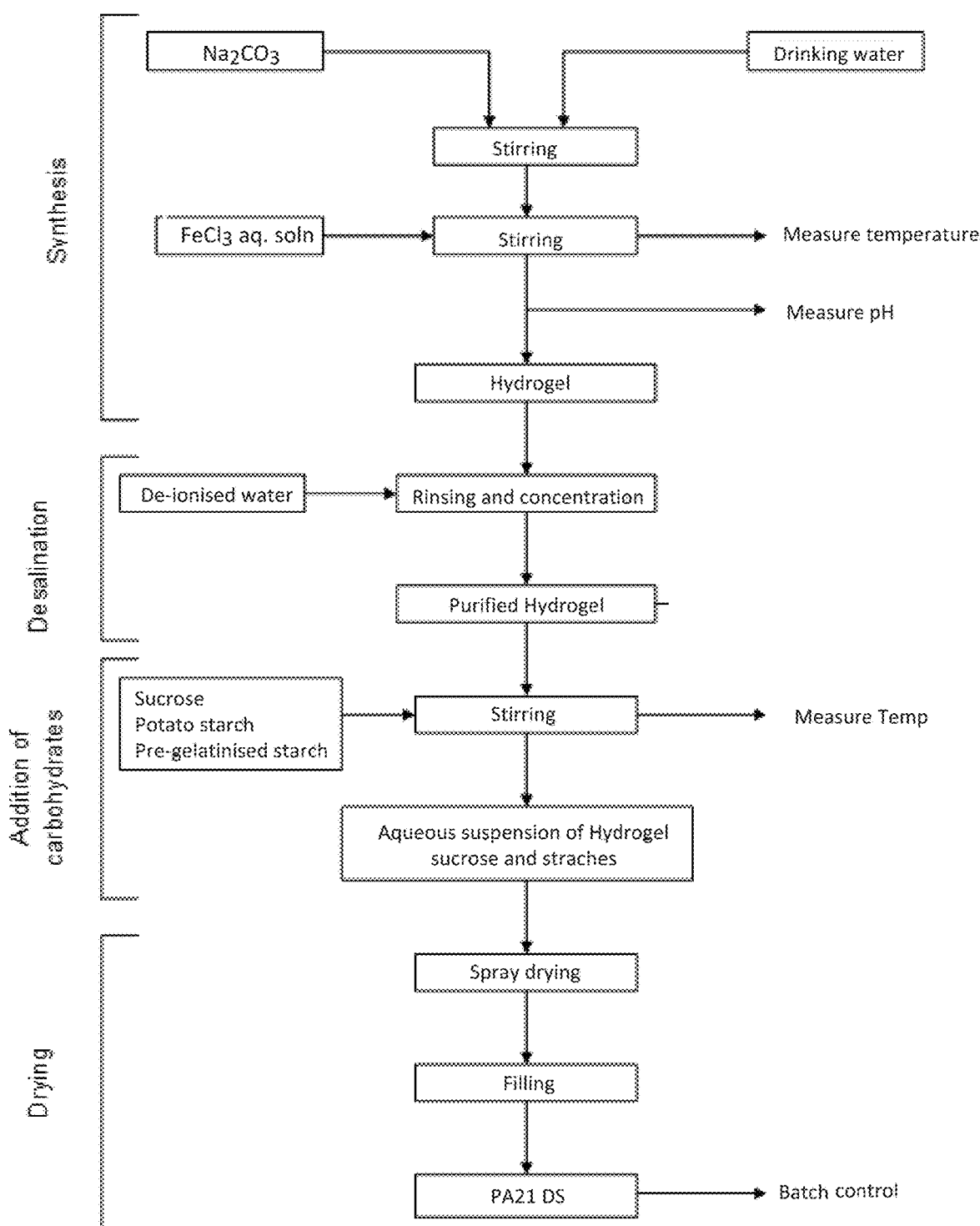

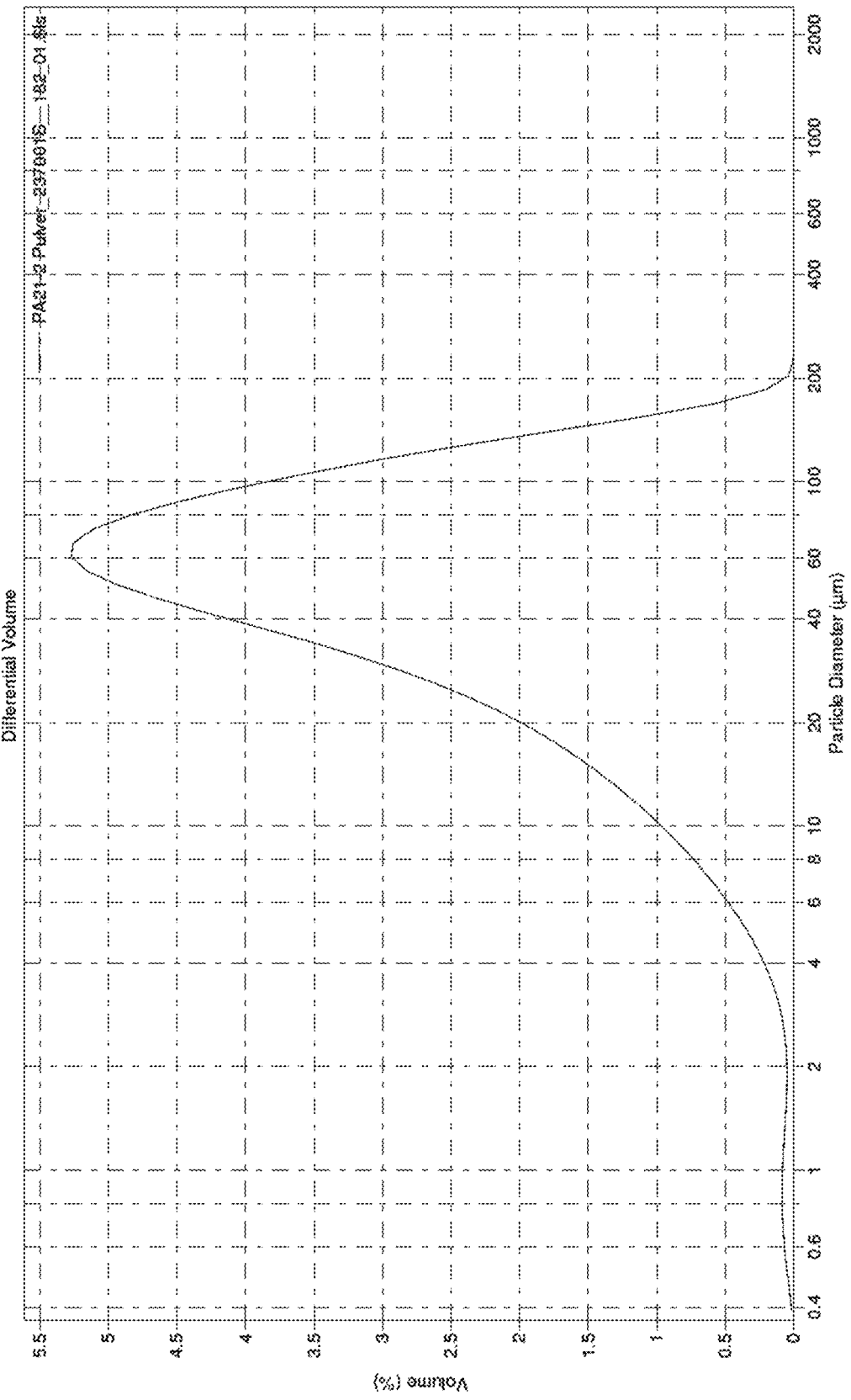
Figure 2 Particle Size Distribution of PA21 Drug Substance analyzed using a Beckman Coulter particle size analyzer (LS 13 320)

Figure 3    Hardness as a function of d50 of the sucroferric oxyhydroxide particles
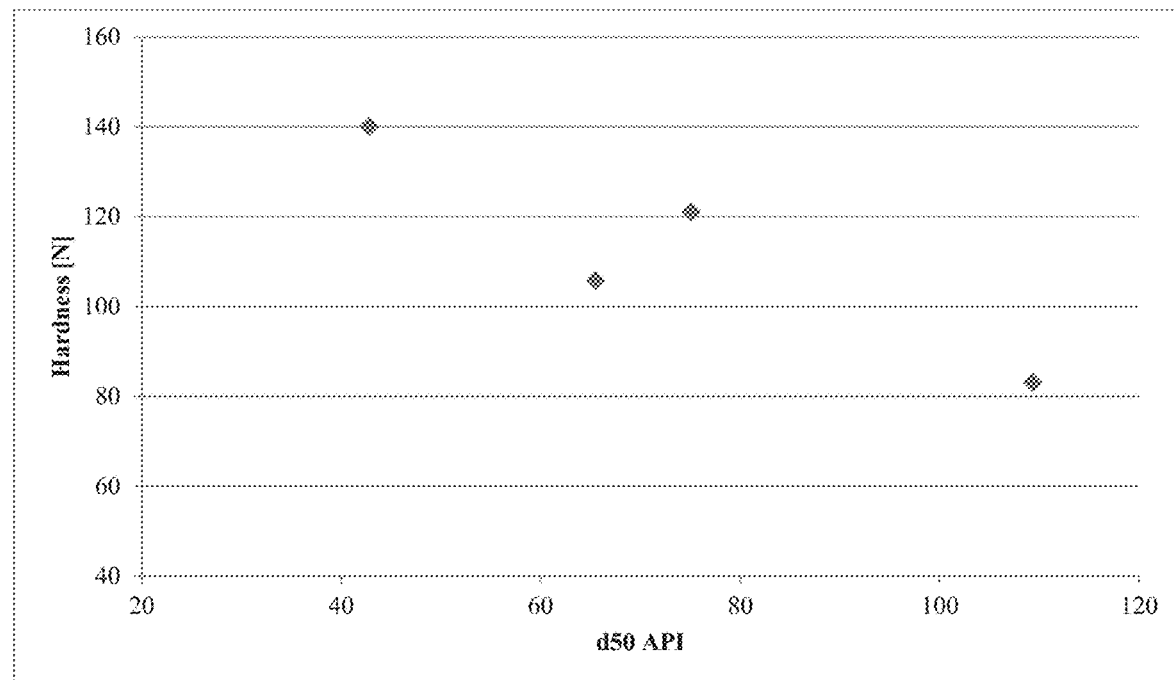
Figure 4    Compression force profile of a tablet with sucroferric oxyhydroxide particles with a d50 of 50 μm
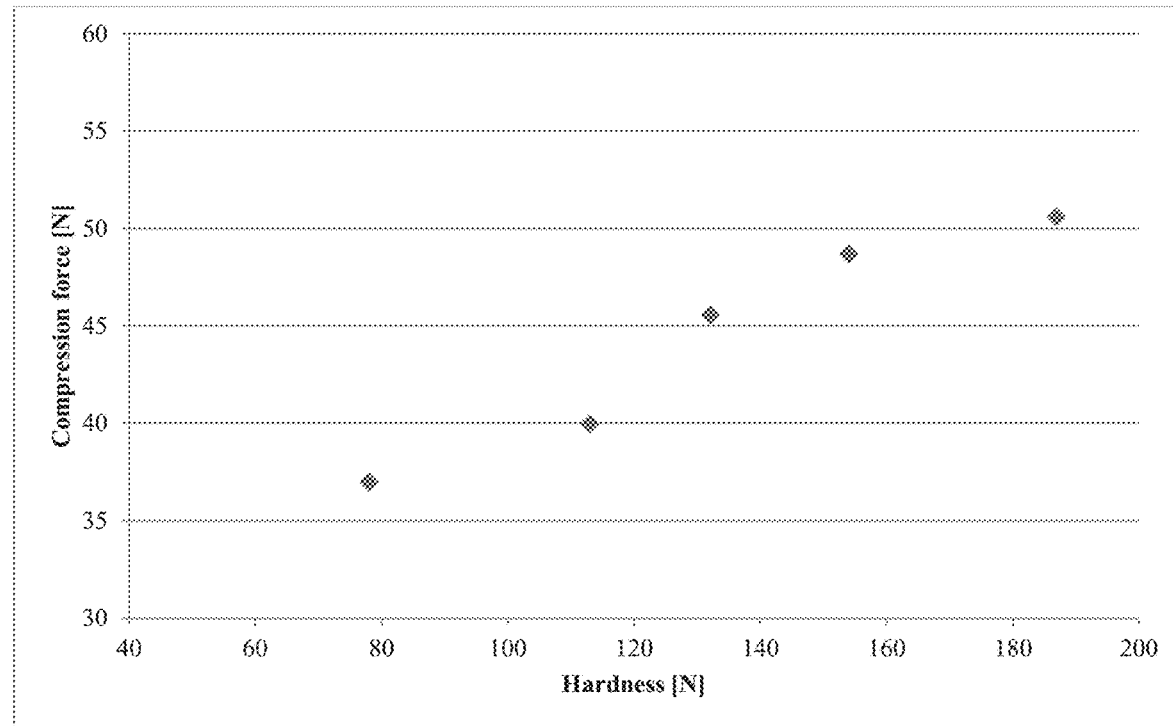

PHARMACEUTICAL COMPOSITION, COMPRISING PHOSPHATE BINDER PARTICLES

BACKGROUND OF THE INVENTION

This invention relates to a pharmaceutical composition comprising a certain phosphate binder, said phosphate binder comprises particles having a certain particle size distribution particularly adapted for the preparation of improved tablets and other pharmaceutical compositions.

WO 20101015827 A2 discloses a ferric iron composition for use in a method of treating hyperphosphatemia, wherein the ferric iron composition is a solid ligand-modified poly oxo-hydroxy metal ion material represented by the formula (MxLy(OH)n), wherein M one or more metal ions that comprise $Fe^{3+}$ ions, L represents one or more ligands that comprise a carboxylic acid ligand, or an ionised form thereof, and OH represents oxo or hydroxy groups and wherein the material has a polymeric structure in which the ligands L are substantially randomly substituted for the oxo or hydroxy groups and wherein the solid ligand-modified poly oxo-hydroxy metal ion material having one or more reproducible physico-chemical properties. While this document mentions certain particle sizes of the solid ligand-modified poly oxo-hydroxy metal ion material, it does not disclose any particle size distribution for a particular pharmaceutical composition, but only a particle size distribution of the freshly prepared phosphate binder materials. Accordingly this document does not teach anything about the relevance of the particle size distribution to be used for a pharmaceutical composition. WO 20101015827 A2 does not contain any example of a specific pharmaceutical composition.

U.S. Pat. No. 5,514,281 relates to a process for the selective reduction of the amount of inorganic phosphate in an aqueous liquid feed containing protein, in addition to said inorganic phosphate, without significantly adversely affecting said protein, which comprises: contacting an aqueous liquid feed, containing phosphate ions and protein, with an adsorbent composition comprising; at least one polynuclear metal oxyhydroxide covalently bound to an adsorbent base material. It mentions some particle sizes of the adsorbent base or support material (e.g. silicate, silicon dioxide, glyceryl modified silicagel, a glyceryl modified glass, and a polymer), but not for the phosphate adsorbent and the polynuclear metal oxyhydroxide. In the examples the phosphate binder is used in an extracorporeal treatment. There is no disclosure of a specific administrable pharmaceutical composition except for known soluble metal oxyhydroxide/polyol complexes.

SUMMARY OF THE INVENTION

This invention relates further to certain pharmaceutical compositions, especially to chewable tablets, tablets, mini-tablets (micro-tablets) formed with and without prior processing like wet granulation or dry granulation (e.g. roller compaction), granulate and tablets especially formed by direct compression of a certain phosphate binder compound (hereinafter phosphate binder), a process for the preparation thereof, new powders comprising the phosphate binders capable of being directly compressed into tablets and or filled into capsules or sachets or other suitable carrier systems (e.g. dispenser for mini tablets). The invention further relates to a process for preparing the pharmaceutical administration form, e.g. by blending the active ingredient and specific excipients into the new formulations and then compressing or directly compressing the formulations into the final form (e.g. direct compressed tablets) or the filling and use in e.g. dispensers or sachets.

The phosphate binders according to the present invention include in particular "iron oxy-hydroxide based stabilized by a stabilization agent" or "stabilized iron oxy-hydroxide phosphate binders" as described in WO9722266 A1 and WO2009062993 A1. The wording "iron oxy-hydroxide, which is stabilized by a stabilization agent" or "stabilized iron oxy-hydroxide phosphate binders", includes preferably an iron oxy-hydroxide together with a stabilization agent, which includes in particular carbohydrates and humic acid. As described in WO9722266 A1 such stabilization agent is suitably not bound as a complex compound to the iron oxy-hydroxide, which means for example that a water-soluble stabilization agent can be removed by washing the stabilized iron oxy-hydroxide with water. As further described in EP WO9722266A1 the stabilization agent is supposed to stabilize the iron oxy-hydroxide structure, and to prevent ageing of the iron oxy-hydroxide, thereby securing and preserving its phosphate adsorption capacity. This means that a stabilized iron oxy-hydroxide (FeOOH) in general has a higher phosphate adsorption capacity (as measured in EP WO9722266 A1) compared to a non-stabilized iron oxy-hydroxide. In accordance with the present invention a preferred "iron oxy-hydroxide, which is stabilized by a stabilization agent" comprises beta iron oxy-hydroxide stabilized as described in WO9722266A1 with at least one carbohydrate and/or humic acid. In accordance with the present invention the iron moiety contains preferably a hydrated polynuclear oxy-hydroxide array "wrapped" by not covalently bond carbohydrates, in particular, sucrose as sugar. The presence of the carbohydrates, in particular, sucrose as sugar is supposed to be essential for the maintenance of the hydrated structure of the polynuclear oxy-hydroxide and therefore for the high phosphate binding capacity. Sucrose and starches are the carbohydrates that are preferably used. The sucrose is supposed to prevent dehydration ("ageing") of the polynuclear iron(III)-oxyhydroxide, and the starches are supposed to improve processability during production. The iron oxy-hydroxide (FeOOH) can be in the form of microcrystals, such as in the form of $\beta$-FeOOH. The repeating moiety of the iron-oxyhydroxide microcrystals can be described by the molecular formula FeOOH. The preferred $\beta$-FeOOH structure (akaganeite) contains anions arranged in a body-centered cubic array with Fe(III) ions occurring on the octahedral sites. The structure consists of double chains of edge-shared octahedral running parallel to the fourfold symmetrical b-axis.

Generally, due to their chemical nature the iron oxy-hydroxides used and administered in accordance with the present invention essentially are not absorbed by the human body.

The term "stabilization agent" as used herein includes preferably at least one carbohydrate and/or humic acid, in particular, as described in WO9722266A1. In one embodiment at least one carbohydrate is soluble in water. Carbohydrates include at least one mono-, di- or polysaccharide, such as agarose, dextran, dextrin, dextran derivatives, cellulose and cellulose derivatives, saccharose (sucrose), maltose or lactose preferably saccharose (sucrose), dextrin or starch.

The term "starch" as used herein includes any conventionally used starch products (such as potato starch, corn starch, rice starch, tapioca starch) in native, pregelatinized, degraded, modified, and derivatized forms, preferably suitable for direct compression, and mixtures thereof. Most preferred products include native and pregelatinized starch, such as in a mixture having a ratio (native-pregelatinized) in the weight-range of 10:1 to 0.5:1, preferably in the range of 3:1 to 0.5:1 more preferably in the range of 2:1 to 1:1.

Preferably the phosphate binder is sucroferric oxyhydroxide (USAN name) or defined by the WHO under the ATC code as V03AE05, or also known as PA21, which is a mixture of iron(III) oxyhydroxide, sucrose, starches.

The preferred phosphate binder comprises polynuclear iron(III)-oxyhydroxide stabilized by sucrose, and starches (known as sucroferric oxyhydroxide or PA21 (PA21-1 or PA21-2)) or a polynuclear β-iron(III)-oxyhydroxide stabilized by sucrose, and starches (known as sucroferric oxyhydroxide or PA21 (PA21-1 or PA21-2)). A particularly preferred mixture of iron(III) oxyhydroxide, sucrose and starches comprises about 25 to 40 wt-% iron(III) oxyhydroxide, about 25 to 40 wt-% sucrose and about 25 to 40 wt-% starches based on the total dry weight (i.e. 100 wt-%) of phosphate binder particles based on such mixture. A particular preferred mixture of iron(III) oxyhydroxide, sucrose and starches comprises about 30 to 35 wt-% iron(III) oxyhydroxide, about 30 to 35 wt-% sucrose and about 30 to 35 wt-% starches based on the total dry weight (i.e. 100 wt-%) of phosphate binder particles based on such mixture, wherein the iron(III) oxyhydroxide preferably comprises β-iron(III) oxyhydroxide.

In the present invention the term "sucroferric oxyhydroxide" covers a mixture of iron(III) oxyhydroxide, sucrose and starches, wherein the mixture comprises one, two or more starches e.g. only native starch (PA21-1) or only pregelatinized starch or a mixture of native starch and pregelatinized starch (PA21-2), etc. A preferred "sucroferric oxyhydroxide" contains a mixture of native starch and pregelatinized starch as herein above defined.

In each case in particular in the claims and the final products of the working examples, the subject matter of the final products, the pharmaceutical preparations and the claims are hereby incorporated into the present application by reference to the herein mentioned publications or patent applications.

As is known to the skilled person in the art "phosphate binders" are compounds or compositions that are capable to act as an adsorbent for phosphate from aqueous medium, for example from aqueous solutions, in particular from physiological aqueous solutions. They are particularly suitable as an adsorbent for inorganic phosphate and phosphate bonded to foodstuffs, especially in a preparation for oral application for the prophylaxis and treatment of hyperphosphatasemia conditions, in particular in patients with chronic renal insufficiency, which have a pathologically increased serum phosphate level due to the decrease in the glomular filtration rate. The term "phosphate binders" according to the present invention covers any salt, isomer, enantiomer or crystal form of such active ingredient.

The phosphate binders, e.g. sucroferric oxyhydroxide, may be combined with one or more pharmaceutically acceptable carriers and, optionally, one or more other conventional pharmaceutical adjuvants and administered enterally, e.g. orally, in the form of tablets, chewable tablets, mini-tablets (micro-tablets), granules, capsules, caplets, granules, powders etc. The enteral compositions may be prepared by conventional means or enabling technologies.

The phosphate binders e.g. sucroferric oxyhydroxide, may be formulated into pharmaceutical compositions containing an amount of the active substance (phosphate binders) that is effective for treating hyperphosphatemia or conditions resulting from unbalanced phosphate levels (e.g. for therapeutic use in the control of serum phosphorous levels in patients with Chronic Kidney Diseases (CKD) who are on dialysis), such compositions comprising a pharmaceutically acceptable carrier, and such compositions being formulated into unit dosage forms or multiple dosage preparations.

In view of their ability to adsorbs the dietary phosphate in the gastrointestinal tract, the phosphate binders, are useful in treating unbalanced phosphate levels and conditions resulting from unbalanced phosphate levels (e.g. for therapeutic use in the control of serum phosphorous levels in patients with CKD who are on dialysis, or treatment of hyperphosphatemia).

The phosphate binders especially sucroferric oxyhydroxide, useful in this invention should preferably not be mixed with humid/wet excipients, and are not inherently compressible. Consequently, there is a need to provide a free-flowing and cohesive pharmaceutical formulations in the form of a powder or granulate, used as such e.g. filled into capsules or sachets or dispensing units, with or without dosing aid, compressed or directly compressed into tablets, chewable tablets, mini-tablets (micro-tablets) or comparable dosage forms.

Tablets may be defined as solid dosage pharmaceutical forms containing one or more drug substances with or without suitable inert materials known as excipients. They are produced by compression of a pharmaceutical formulation, in the form of a powder or granules or smaller dosing units (e.g. mini-tablets, pellets), containing the phosphate binder and certain excipients. Without excipients most drugs and pharmaceutical ingredients cannot be directly-compressed into tablets. This is primarily due to the poor flow and cohesive properties of most drugs.

There has been widespread use of tablets and the majority of pharmaceutical dosage forms are marketed as tablets. Major reasons for tablet and chewable tablet popularity as a dosage form are simplicity of use, low cost and the speed of production. Other reasons include stability of drug product, convenience in packaging, shipping and dispensing. To the patient or consumer, tablets offer convenience of administration, ease of accurate dosage, compactness, portability, blandness of taste, and ease of administration.

Tablets may be plain, film or sugar coated bisected, embossed, layered or sustained-release. They can be made in a variety of sizes, shapes and colors. Tablets may be swallowed, chewed or dissolved in the buccal cavity or beneath the tongue. They may be dissolved in water for local or topical application.

Other desirable characteristics of excipients and active ingredients include the following:
  High-compressibility to result strong tablets at low compression forces;
  Narrow particle size distribution;
  Good flow properties that can improve the flow of other components in the formula; and
  Cohesiveness (to prevent tablet from crumbling during processing, shipping and handling).

There are four commercially important processes for making compressed tablets: wet granulation followed by compression, direct compression, dry granulation (slugging or roller compaction) followed by compression and extrusion (e.g. melt extrusion) followed by compression. The method of preparation and the type of excipients used are tailored to give the tablet formulation the desired physical characteristics that allow for the rapid compression of the tablets. After compression, the tablets must fulfill a number of attributes, such as e.g. appearance, hardness, disintegration time, friability, uniformity of mass, chewability, and dissolution profile. Choice of fillers and other excipients will depend on the chemical and physical properties of the drug, behavior of the mixture during processing and the properties of the final tablets.

The properties of the drug, its dosage forms and the economics of the operation will determine selection of the best process for tableting.

The dry granulation method may be used where one of the constituents, either the drug or an excipient, and/or the mixture thereof has sufficient cohesive properties to be compacted. The method consists of blending, slugging the ingredients, compaction, dry screening, lubrication and compression.

The wet granulation method is used to convert a powder mixture into granules having suitable flow and cohesive properties for tableting. The procedure consists of mixing the powders in a high-shear granulator followed by adding the granulating solution under shear to the mixed powders to obtain a granulation or to add the liquid by spraying in a fluid bed dryer to result the granulate. The damp mass may be screened through a suitable screen and dried by tray drying or other suited drying techniques. The overall process may include weighing, dry powder blending, wet granulating, drying, milling, blending lubrication and compression.

Typically drug substance powders do not have sufficient adhesive or cohesive properties to form hard, strong granules. A binder is usually required to form larger particles (granules). Heat and moisture sensitive drugs mostly cannot be manufactured using wet granulation. The drawback of this the wet granulation technology is the number of processing steps and needed processing time materializing in the manufacturing costs.

Direct compression is regarded as preferred process where the solid components are compressed directly without changing the physicochemical properties of the drug. The active ingredient(s), direct compression excipients and other auxiliary substances, such as a glidant and lubricant are blended in a bin blender before being compressed into tablets. The advantages of the direct compression technology include e.g. the uniformity of the blend, few manufacturing steps involved, i.e., the overall process involves weighing of powders, blending and compression, hence limited cost; eradication of heat and moisture, prime particle dissociation and physical stability.

Pharmaceutical manufacturers do prefer to use direct compression techniques over wet or dry granulation methods because of the short processing time and limited process steps resulting in advantageous cost. Direct compression however is usually limited to cases where the active ingredient has acceptable physicochemical characteristics required to form a pharmaceutically acceptable dosage form. Many active ingredients do no exhibit all necessary properties and therefore often must be combined with suited excipients to allow for direct compression. Since each excipient added to the formulation increases the tablet size of the final product, manufacturers are often limited to using the direct-compression method in formulations containing a low dose of the active ingredient per compressed tablet.

A solid dosage form containing a high-dose drug, i.e. the drug itself comprises a substantial portion of the total compressed tablet weight, can only be directly compressed if the drug itself has appropriate physical characteristics, e.g. cohesiveness, to be directly compressed.

The claimed pharmaceutical composition, comprising phosphate binders especially sucroferric oxyhydroxide is considered a high-dose drug i.e. high-dose of sucroferric oxyhydroxide per unit dosage form (e.g. per tablet). Unit dosage formulations can include above 60%, 70%, 80%, or 90% and more by weight of the phosphate binder per unit dosage form (e.g. per tablet). A single oral dosage form of the phosphate binders especially sucroferric oxyhydroxide shall contain preferably more than 400 mg, or more than 800 mg or more than 1000 mg or more than 1500 mg or more than 2000 mg or 2500 mg of phosphate binder. This high-dose drug, combined with its rather poor physical characteristics for direct compression, has not permitted the use of the direct compression technology to prepare the final product with acceptable physical characteristics. The phosphate binders are relatively unstable in the presence of free water (or have poor microbiological stability), a factor militating against the use of the wet granulation technology (the large amount of phosphate binder in an adequate single dose formulation would require too much water).

Earlier used tablets comprising sucroferric oxyhydroxide, such as described in the patent application WO2009/062993 did only partially meet the expected physical characteristics e.g. still remaining potential cohesiveness issues. Tablets could more easily break, and had still not an acceptable friability or hardness or compressibility or chewability or disintegration time or dissolution profiles.

As patients suffering from unbalanced phosphate levels (e.g. patients with CKD (Chronic Kidney Diseases) who are on dialysis) need to be administered with several oral dosage forms per day, over several months or years, there is a clear need for improvement of the oral dosage forms e.g. improved physical characteristics.

All % weights (w/w) throughout this description are expressed in relation to the total weight of the pharmaceutical composition (dry composition), if not indicated otherwise.

Another limitation of direct compression as a method of tablet manufacturing is the potential size of the compressed tablets. The amount of excipients needed in wet granulation is less than that required for direct compression since the process of wet granulation contributes toward the desired physical properties of the tablet.

Therefore, if the amount of active ingredient is high, a pharmaceutical formulator may choose to wet granulate the active ingredient with other excipients to attain an acceptable sized tablet with the desired amount of active ingredient. As herein described, the phosphate binders especially sucroferric oxyhydroxide is preferably administered to the patients as single dosage form, wherein said dosage form contains a high drug load of phosphate binder. Furthermore, due to the behavior of the claimed phosphate binders in the presence of water, it is desirable to perform direct compression of tablets containing high-dose phosphate binders especially sucroferric oxyhydroxide. Therefore, there is strong technical hurdles which need to be overcome in order to manufacture compressed (or direct compressed) big sized tablets which exhibit acceptable friability, hardness, chewability, cohesiveness, disintegration time and dissolution profiles.

Depending on the intended use of the tablet, i.e. whether it is for intact swallowing or rapid disintegration (in the oral cavity or in a small amount of liquid prior to ingestion) or to be chewed, such as e.g. a chewable tablet, usually excipients, such as disintegrants, superdisintegrants, glidants, lubricants, binder compression aids and the like may be added if desired. The tablet may be coated or not, as pharmaceutically necessary or desired.

Thus, the pharmaceutical composition of the invention includes any dosage form suitable for oral administration and in particular may include tablets (preferably direct compressed tablets and pills, either in a form for intact swallowing (e.g. also film-coated) or in a form capable of rapid disintegration (either in the oral cavity after ingestion or in a small amount of liquid prior to ingestion), including chewable forms, mini tablets, dry powders, granules, capsules or sachets containing these granules or mini-tablets (micro-tablets), wafers, lozenges, and the like. The form for intact swallowing may be film-coated, if desired. The pharmaceutical composition of the invention includes also powders or granules which can be compressed or compacted into tablets.

Preferred dosage forms include tablets and pills, either in a form for intact swallowing (e.g. film-coated) in or in a chewable form, granules and capsules or sachets containing these granules, and lozenges. In the case of orally administrate dosage forms, if desired film-coated, these are swallowed intact and disintegration takes place in the stomach or/and other parts of the intestine, whereupon the active agent is released for adsorption of phosphate to reduce its systemic uptake.

With the herein claimed pharmaceutical formulations, compositions, and tablets, the administration can be at as minimal as 3 to 4 unit dosage forms per day.

As herein described, the phosphate binders especially sucroferric oxyhydroxide is preferably administered to the patients in the form of a single dosage form per administration, wherein said dosage form contains a high load of phosphate binder i.e. more than 400 mg or more than 800 mg or more than 1000 mg or more than 2000 or more than 2500 mg of phosphate binders, preferably between 1500 to 3000 mg or between 2000 to 3000 mg of phosphate binders. Dependent on the API load, the choice of appropriate solid dosage form is limited. The most common options to result unit dosage forms with high drug substance content are: powder/granulate/minitablet filled sachets, effervescent tablets or chewable tablets. Chewable tablets offer the advantage of more flexibility in not requiring access to water and in the fact that the medication can be more discretely taken, i.e. at work, while travelling or at social occasions. In addition, avoiding additional water intake is of advantage for the patient group with CKD (Chronic Kidney diseases). Also, surveys indicate that patients prefer to take a single dose e.g. a tablet per administration instead of multiple dose like it would be required with swallowable tablets or tablet with smaller size for high dosed medications. The mechanical strength of chewable tablets can however be of concern with regard to damage to teeth or mandibular joints from chewing tablets with unsuitable mechanical properties. As CKD patients have to chew several tablets per day for several months or years, the chewability of the tablets is critical. Several testing procedures and additional methods with the objective of obtaining a meaningful evaluation of the chewability of tablets and confirming the appropriateness of the phosphate binder selected formulations/tablets from the chewability perspective were applied.

In the present invention the "pharmaceutical compositions" comprise the phosphate binder compound as active ingredient (preferably one, two or three) and preferably at least one pharmaceutically acceptable excipient, which can be in the form of a powder (to be incorporated into sachet or capsules, preferably a dry powder), of tablets (compressed into tablets, preferably mono, bi or tri layer tablet), pills, granules or micro granules, capsules, pellets, wafers, lozenges or coated tablet.

In the present invention, the term "granules" do also cover micro-granules. The granules can be used for direct administration or further processed into tablets, mini-tablets, chewable tablets.

In the present invention, the term "tablet" covers any type of tablet resulting from the compression or compaction of powders, granules (obtained by wet or dry granulation, tableting, melt extrusion), mini-tablets, micro granules, pellets, but refers preferably a direct compressed tablet.

In the present invention the term "compressed" covers any physical compaction process resulting in solid dosage units.

In the present invention, the term "pharmaceutical formulations (or formulations)" covers mixture of active ingredients (preferably one, two or three) and pharmaceutically acceptable excipients, which are in a form adapted to the preparation/manufacturing of a pharmaceutical product (e.g. pharmaceutical composition). In the present invention the preferred formulations are powders or granules adapted for compaction or compression or direct compression into tablets.

It is also an object of the invention to provide phosphate binders as hereinafter described, in the form of a pharmaceutical formulation, preferably in the form of a free-flowing, cohesive tableting powder (powder formulation), capable of being compressed or directly compressed into a tablet.

It is also an object of the invention to provide a phosphate binder as hereinafter described, in the form of a pharmaceutical formulation, preferably in the form of tableting granules (obtained by wet or dry granulation or melt extrusion) which can be mixed with further excipients, capable of being compacted, compressed or directly compressed into a tablet.

It is a further object of the invention to provide a compressed (or directly compressed) phosphate binder tablet in unit dosage form having an acceptable dissolution profile, as well as acceptable degrees of hardness and resistance to chipping, as well as acceptable friability and chewability profiles, as well as a fast disintegration time.

It is a further object of the invention to provide a compressed (or preferably direct compressed) phosphate binder tablet which is a rapid disintegration tablet (in the oral cavity or in a small amount of liquid prior to ingestion), like e.g. a chewable tablet or mini tablets.

It is a further object of the invention to provide a process for preparing a compressed phosphate binder tablet by direct compression in a unit dosage forms.

The present invention also provides a tableting, free-flowing particulate phosphate binder composition in the form of a tableting powder (comprising preferably at least one additional pharmaceutically acceptable excipient as herein after described), capable of being compressed, or directly compressed into a tablet having adequate hardness, friability, chewability, rapid disintegration time and an acceptable dissolution pattern.

BRIEF DESCRIPTION OF THE DRAWINGS

The present invention will be described in greater detail with reference to the accompanying drawings in which FIG. 1 schematically illustrates a flowchart for manufacturing the phosphate binder particles according to the present invention, FIG. 2 illustrates a graph of particle size distribution analyzed in the phosphate binder particles according to the present invention, FIG. 3 illustrates a graph of hardness of the phosphate binder particles according to the preset invention, and FIG. 4 illustrates a graph of compression force of a tablet including the phosphate binder particles according to the present invention.

DETAILED DESCRIPTION

In the development of the herein described pharmaceutical compositions the applicant has discovered that it is particularly advantageous to use a pharmaceutical composition, especially in the form of a tablet, preferably a compressed tablet, comprising a phosphate binder, said phosphate binder comprises particles having a particle size distribution, wherein at least 40% of the particles have a particle size within the range of 4 to 200 µm.

Preferably:
i) the particles of the phosphate binder especially of sucroferric oxyhydroxide, have a particle size distribution with particles in the range of 4 to 200 µm, preferably wherein at least 40% (by volume) of the particles have a particle size in the range of 4 to 200 µm, and/or
ii) the phosphate binder particles especially the sucroferric oxyhydroxide particles have a d50 in the particle size distribution which is in the range of 30 µm to 120 µm, or 35 µm to 110 µm, or 40 µm to 108 µm, or 40 µm to 100 µm, or preferably of 40 µm to 80 µm, or 42 µm to 75 µm, and/or
iii) the hardness of the tablets is between 70 to 250 N or 85 to 250 N or 85 to 200N or 70 to 200 N or 80 to 200 N, and/or
iv) the tablet friability is between 0% to 7% or between 0.05% to 7%, and/or
v) the tablet has a disintegration time of less than 30 min, preferably between 5 and 20 min, and/or
vi) the tablet diameter is between 15 mm to 30 mm, the tablet weight is between 2000 mg to 3000 mg and the tablet thickness is between 4.5 mm and 7.5 mm.

In particular, the present invention concerns a pharmaceutical composition or a compressed pharmaceutical tablet preferably a direct compressed tablet, comprising a phosphate binder. Said phosphate binder, especially sucroferric oxyhydroxide, has unfavorable physical properties to be converted into an acceptable compressed preferably direct compressed pharmaceutical tablet. These unfavorable physical properties can be e.g. bulkiness, sticking, fluffiness and the like. During development of the herein described pharmaceutical compositions and tablets, the applicant has discovered that the processing properties or physical properties of the pharmaceutical formulation, such as hygroscopicity, flowability, bulkiness, fluffiness is unexpectedly improved if the particles comprising the phosphate binder especially sucroferric oxyhydroxide have a particle size distribution wherein at least 40%, or at least 60%, or at least 80%, or at least 90% by volume is in the range of 4 to 200 µm (preferably in the range of 5 to 160 µm) and/or a d50 (related to the volume of the particles) in the particle size distribution in the range of 30 µm to 120 µm or 35 µm to 110 µm or 40 µm to 108 µm or 40 µm to 100 µm, or preferably of 40 µm to 80 µm (preferably in the range of 42 µm to 75 µm). The applicant also surprisingly discovered that the tablets show improved physical characteristics such as solubility, friability, hygroscopicity, hardness, compressibility, chewability, or disintegration.

An additional unexpected advantage of the selected particle size distribution, is the possibility to increase the compression force during the tableting process, without any alterations (except hardness) of the tablet physical properties but with the possibility to increase the tablet hardness to the targeted hardness range.

In a preferred first embodiment (a) the present invention concerns compressed tablets preferably direct compressed pharmaceutical tablets, wherein the powder to be compressed contains particles comprising a phosphate binder (the phosphate binder particles) especially sucroferric oxyhydroxide, and at least one further pharmaceutically acceptable excipient, and wherein at least 40%, preferably 60%, most preferably 80% even more preferably 90% (by volume) of the particles of the phosphate binder particle size distribution in the tablet are between 4 to 200 µm or between 5 to 160 µm or between 21 to 160 µm.

In a preferred second embodiment (b) the present invention concerns compressed tablets preferably direct compressed pharmaceutical tablets, wherein the powder to be compressed contains particles comprising a phosphate binder (the phosphate binder particles) especially sucroferric oxyhydroxide, and at least one further pharmaceutically acceptable excipient, and wherein the phosphate binder particles have a d50 (by volume) in the particle size distribution in the range of 30 µm to 120 µm, or 35 µm to 110 µm, or 40 µm to 108 µm, or 40 µm to 100 µm, or preferably of 40 µm to 80 µm or preferably in the range of 42 µm to 75 µm.

In a preferred third embodiment (c) the present invention concerns compressed tablets preferably direct compressed pharmaceutical tablets, wherein the dispersion contains particles comprising a phosphate binder (the phosphate binder particles) especially sucroferric oxyhydroxide and at least one further pharmaceutically acceptable excipient, and wherein:
i) at least 40%, preferably 60%, most preferably 80% even more preferably 90% (by volume) of the particles in the phosphate binder particle size distribution are between 4 to 200 µm or between 5 to 160 µm or between 21 to 160 µm, and
ii) the phosphate binder particles have a d50 (by volume) in the particle size distribution between 30 µm to 120 µm, or 35 µm to 110 µm, or 40 µm to 108 µm, or 40 µm to 100 µm, or preferably of 40 µm to 80 µm or preferably between 42 µm to 75 µm, and/or
iii) the hardness of the tablets is between 70 to 250 N, and/or
iv) the tablets friability is between 0% to 7% or 0.05% to 7%, and/or
v) the tablet has a disintegration time of less than 30 min, preferably between 5 and 20 min, and/or
vi) the tablet diameter is between 16 mm to 30 mm, the tablet weight is between 1500 mg to 3000 mg (preferably 2000 to 3000 mg) and the tablet thickness is between 4.5 mm and 7.5 mm, and/or,
vii) the tablet contains between 1500 mg to 3000 mg of phosphate binder especially sucroferric oxyhydroxide.

In a preferred fourth embodiment (d) the present invention concerns a a pharmaceutical composition, which contains particles comprising a phosphate binder especially sucroferric oxyhydroxide and at least one further pharmaceutically acceptable excipient, and wherein the phosphate binder particles have a d50 in the particle size distribution between 30 µm to 120 µm, or 35 µm to 110 µm, or 40 µm to 108 µm, or 40 µm to 100 µm, or preferably of between 40 µm to 80 µm or between 42 µm to 75 µm, wherein d50 relates to the volume of the particles.

In a preferred fifth embodiment (e) the present invention concerns a pharmaceutical composition, which contains particles comprising a phosphate binder especially sucroferric oxyhydroxide and at least one further pharmaceutically acceptable excipient, and wherein at least 40%, preferably at least 60%, or preferably at least 80%, or at least 90% (by volume) of the particle size distribution in the formulation or composition is between 4 to 200 µm or between 5 to 160 µm or between 21 to 160 µm.

The term "wherein at least 40%, preferably at least 60%, or at least 80%, or at least 90%" means that at least 40%, preferably at least 60%, or at least 80%, or at least 90% of the particles (phosphate binder particles) are of the said size i.e. belong to the said size range. The percentages are volume-%.

The term "d50 particle size distribution" means that 50% (per volume) of the particles have a particle size above or below the defined d50 value expressed in µm.

The term "d10 particle size distribution" means that 10% (per volume) of the particles have a particle size lower than the d10 value expressed in µm.

The term "d90 particle size distribution" means that 90% (per volume) of the particles have a particle size lower than the d90 value expressed in µm.

These d-values relate in particular to the cumulative particle volume in the particle distribution curve.

The combination of the above third embodiment (c) parameters provide compressed tablets preferably direct compressed tablets with particularly improved physical characteristics as herein above defined.

Thus this invention concerns also compressed tablets (e.g. a chewable tablet), preferably direct compressed tablets, which contains particles comprising a phosphate binder (the phosphate binder particles) especially sucroferric oxyhydroxide and at least one further pharmaceutically acceptable excipient and wherein one or more of the following features i) to vii) is met:
   i) at least 40%, preferably at least 60%, or preferably at least 80%, or at least 90% (by volume) of the particles of the phosphate binder particle size distribution in the tablet are between 4 to 200 µm or between 5 to 160 µm or between 21 to 160 µm,
   ii) the phosphate binder particles have a d50 (especially by volume) in the particle size distribution between 30 µm to 120 µm, or 35 µm to 110 µm, or 40 µm to 100 µm, or preferably of between 40 µm to 80 µm or between 42 µm to 75 µm,
   iii) the hardness of the tablets is between 70 to 250 N,
   iv) the tablets friability is between 0% to 7% or between 0.05% to 7%,
   v) the tablets have a disintegration time of less than 30 min, preferably between 5 and 20 min,
   vi) the tablet diameter is between 16 mm to 30 mm and the tablet weight is between 2000 mg to 3000 mg and the tablet thickness is between 4.5 mm and 7.5 mm,
   vii) the tablet contains between 1500 mg to 3000 mg of phosphate binder especially sucroferric oxyhydroxide.

In a further embodiment, this invention concerns any of the herein described compressed tablets, wherein the hardness of the tablets is between 85 to 250 N or between 70 and 200 N or 85 to 200 N, or between 85 to 200 N or between 80 to 200 N or between 100 N to 230 N.

In a preferred embodiment, this invention concerns any of the herein described compressed tablets preferably direct compressed pharmaceutical tablets, preferably chewable tablets.

In a preferred embodiment, this invention concerns a chewable tablet as hereinabove described, wherein; i) the phosphate binder is sucroferric oxyhydroxide, and ii) the tablet contains between 1500 mg to 3500 mg or between 2000 to 3000 mg of sucroferric oxyhydroxide.

Preferably the phosphate binder particles in the formulation or tablets especially the sucroferric oxyhydroxide phosphate binder particles as herein described, represent more than 65% of the total tablet mass (total tablet weight), preferably more than 80% or more than 90% or even more than 95% of the total mass of the tablets (by weight on a dry weight basis) or of the formulation.

As described above the preferred phosphate binder to be used in the pharmaceutical compositions according to the invention comprises polynuclear iron(III)-oxyhydroxide stabilized by sucrose, and starches (known as sucroferric oxyhydroxide or PA21) or a polynuclear β-iron(III)-oxyhydroxide stabilized by sucrose, and starches (known as sucroferric oxyhydroxide or PA21). Accordingly the particles of sucroferric oxyhydroxide, i.e. consisting essentially of polynuclear iron(III)-oxyhydroxide, sucrose, and starches have a particle size distribution wherein at least 40%, or at least 60%, or at least 80%, or at least 90% by volume is in the range of 4 to 200 µm (preferably in the range of 5 to 160 µm) and/or a d50 (related to the volume of the particles) in the particle size distribution in the range of 30 µm to 120 µm or 35 µm to 110 µm or 40 µm to 108 µm or 40 µm to 100 µm, or preferably of 40 µm to 80 µm (preferably in the range of 42 µm to 75 µm). A particularly preferred mixture of iron(III) oxyhydroxide, sucrose and starches comprises about 25 to 40 wt-% iron(III) oxyhydroxide, about 25 to 40 wt-% sucrose and about 25 to 40 wt-% starches based on the total dry weight (i.e. 100 wt-%) of the phosphate binder particles of such mixture. A particular preferred mixture of iron(III) oxyhydroxide, sucrose and starches comprises about 30 to 35 wt-% iron(III) oxyhydroxide, about 30 to 35 wt-% sucrose and about 30 to 35 wt-% starches based on the total dry weight (i.e. 100 wt-%) of phosphate binder particles of such mixture, and the iron(III) oxyhydroxide preferably comprises β-iron(III) oxyhydroxide.

Accordingly the sucroferric oxyhydroxide phosphate binder particles as herein described are the preferred active ingredient particles (i.e. particles of polynuclear iron(III)-oxyhydroxide stabilized by sucrose, and starches), before mixing such particles with other excipients. Preferably the sucroferric oxyhydroxide particles comprise more than 95% or even more than 98% of sucroferric oxyhydroxide, by weight on a dry weight basis of the particles (i.e. of the drug substance particles before mixture with additional excipients). Preferably not more than 2% to 5% of side products or impurities resulting from manufacturing process should be present in the sucroferric oxyhydroxide particles (e.g. sodium chloride etc.). Active ingredient particles can also be named drug substance (DS) particles.

Preferably the phosphate binder particles in the tablets or pharmaceutical compositions, especially the sucroferric oxyhydroxide phosphate binder particles as herein described, represent more than 65%, preferably more than 80%, or preferably more than 90% and even more than 95% of the total weight of the tablet or of the pharmaceutical composition (by weight on a dry weight basis).

Phosphate binder particles especially the sucroferric oxyhydroxide particles can be formed by spray drying or an alternative size increasing process well known in the field like e.g. granulation, direct compression etc. microgranulation.

Preferably the sucroferric oxyhydroxide particles comprise more than 65% of sucroferric oxyhydroxide, preferably more than 80% or preferably more than 90% or even more than 95% or even more than 98% of sucroferric oxyhydroxide, by weight on a dry weight basis.

In a further embodiment the inventions relates to the herein described tablets or pharmaceutical compositions, wherein the single oral dosage form of the phosphate binders especially sucroferric oxyhydroxide shall contain preferably more than 400 mg, or more than 800 mg or more than 1000 mg or more than 1500 mg or more than 2000 mg or more than 3000 mg of phosphate binder.

In a further embodiment the inventions relates to the herein described tablets or pharmaceutical compositions, wherein the single oral dosage form of the phosphate binders especially sucroferric oxyhydroxide, contains between 800 mg to 3500 mg of sucroferric oxyhydroxide, or between 1500 mg to 3500 mg of sucroferric oxyhydroxide, or between 1500 mg to 3000 mg of sucroferric oxyhydroxide, or between 2000 mg to 3000 mg of sucroferric oxyhydroxide.

The invention also relates to the herein described tablets or pharmaceutical compositions, wherein the phosphate binder particles have a d50 in the particle size distribution of between 40 µm to 80 µm and wherein at least 60%, most preferably at least 80% (by volume) of the particles of the phosphate binder particle size distribution in the tablet is in between 4 to 200 µm or in between 5 to 160 µm or in between 21 to 160 µm.

It has been discovered that the selected particle size distribution of the phosphate binder especially sucroferric oxyhydroxide are particularly important to enable the compaction of the tablets as hereinabove described, among other advantages.

In a preferred embodiment, the phosphate binder according to the present invention is a polynuclear iron(III)-oxyhydroxide stabilized by sucrose based phosphate binder including a polynuclear iron(III)-oxyhydroxide stabilized by sucrose and one or more starches, including natural starches (potato starch, corn starch etc.) and processed starches like pregelatinized starches.

In a further embodiment the present invention relates to a pharmaceutical composition comprising sucroferric oxyhydroxide particles and optionally at least one further pharmaceutically acceptable excipient, wherein:
  i) at least 40% or at least 60%, at least 80%, or at least 90% (by volume) of the sucroferric oxyhydroxide particles in the particle size distribution are between 4 to 200 µm or in between 5 to 160 µm or in between 21 to 160 µm,
  ii) the sucroferric oxyhydroxide particles have a d50 (by volume) in the particle size distribution of between 30 µm to 120 µm, or 35 µm to 110 µm, or 40 µm to 100 µm, or preferably of between 40 µm to 80 µm,
  iii) sucroferric oxyhydroxide as defined above represents more than 80% or more than 90%, or more than 95%, or more than 97% of the sucroferric oxyhydroxide particles, by weight on a dry weight basis.

If there are further excipients in addition to the phosphate binder particles the particle size distribution of the selected further excipients comprised in the pharmaceutical formulation or a pharmaceutical composition or tablets is similar to the particle size distribution of the phosphate binder particles preferably the sucroferric oxyhydroxide particles. The term "similar" means that the particle size distribution of the excipients in the tablet comprises particles in the range of 5 to 400 µm, or between 5 to 300 µm, preferably between 1 to 200 µm. Preferably at least 40% or at least 60%, at least 80%, or at least 90% (by volume) of the excipient particles are in the range of 5 to 400 µm, or between 5 to 300 µm, preferably between 1 to 200 µm.

The preferred excipients with an adapted particle size distribution can be selected by use of e.g. the "Handbook of Pharmaceutical Excipients ($6^{th}$ edition), edited by Raymond C Rowe-Publisher: Science and Practice".

Particle size of phosphate binders, e.g. sucroferric oxyhydroxide particles size, can be controlled by crystallization, drying, preferably spray drying, compaction and/or milling/sieving (non limiting examples are described below). Producing the desired particle size distribution is well known and described in the art such as in "Pharmaceutical dosage forms: volume 2, 2nd edition, Ed.: H. A. Lieberman, L. Lachman, J. B. Schwartz (Chapter 3: SIZE REDUCTION)". According to the present invention the desired particle size distribution in particular for the preferably used sucroferric oxyhydroxide particles is obtained by a spray drying process, which comprises the step of spray-drying an aqueous suspension of the phosphate binder particles (being comprised of a mixture of iron(III) oxyhydroxide, sucrose, starches in case of the preferred sucroferric oxyhydroxide), wherein the aqueous suspension of the phosphate binder particles is subjected to atomization prior to spray-drying. Atomization of the feed might be generally achieved by basic feed devices of the single fluid nozzle or pressure type, of the two-fluid nozzle or pneumatic type, and of the centrifugal (spinning disc) type. In the present invention atomization is preferably done with the centrifugal (spinning disc) type atomizer. Centrifugal atomization achieves dispersion by centrifugal force, with the feed liquor being pumped to a spinning disc. In the present invention in particular spray drying on an Anhydro Spray drying plant type CSD No. 73 was found to result in an appropriate drying process. For the atomization of the concentrated aqueous PA21 suspension a centrifugal atomizer CE 250 can be used, that atomizes by feeding the liquid feed onto a high-speed wheel. With a rotary atomizer, it is possible to adjust the wheel speed and thereby the particle size better than with a nozzle. Further, rotary atomization is better suited for a shorter spray dryer. The powder received from the spray drying process should have a good flowability and the particle size of the dried product should not be too small. With the rotary atomizer, the particle size can be adjusted in particular by variation of the wheel speed. The wheel speed of the atomizer defines the size of the drops which fall into the drying chamber of the spray dryer. The size of the drops influences the particle size of the dried powder as well as its loss on drying. A higher wheel speed produces smaller drops resulting in a smaller particle size of the dried powder and a lower loss on drying, because a smaller drop contains less water which is faster vaporized during its way through the drying chamber. Since the correlation between the wheel speed and the particle size depends on the chamber geometry, it has to be adapted for each individual plant. For the geometry of the preferred Anhydro Spray drying plant type CSD No. 73 used a wheel speed of between 12000 and 20000 rpm, was found to be suitable for achieving desired particle size distribution. The inlet temperature of the air defines the drying energy which is brought into the spray dryer. Together with the inlet gas flow it defines the drying capacity. The inlet gas flow was kept constant at about $1.9 \times 10^4$ m$^3$/h. The inlet temperature was found suitable in the range of 130-180° C. for the Anhydro Spray drying plant type CSD No. 73.

The desired particle size distribution in particular for the preferably used sucroferric oxyhydroxide particles can be obtained from any form of the phosphate binder especially from any physicochemical form of the sucroferric oxyhydroxide (e.g. different secondary structures such as amorphous or crystalline forms).

Multiple particle sizes have been studied and it has been discovered that the herein described specific size range provides unexpected good results for compression, preferably direct compression and especially for chewable tablets.

Particle size distributions might be measured using Sieve analysis, or laser diffraction (international standard ISO 13320-1), or electronic sensing zone, light obstruction, sedimentation or microscopy which are procedures well known by the person skilled in the art. Sieving is one of the oldest methods of classifying powders by particle size distribution. A further method includes the determination of the volume particle size distribution by TEM (see e.g. Clariant Analytical Services TECHNICAL SHEET 106 TEM-Partikelgröße). Such methods are well known and described in the art such as in any analytical chemistry text book or by the United State Pharmacopeia's (USP) publication USP-NF (2004-Chapter 786-(The United States Pharmacopeial Convention, Inc., Rockville, Md.)) which describes the US Food and Drug Administration (FDA) enforceable standards. The used techniques are e.g. described in Pharmaceutical dosage forms: volume 2, 2nd edition, Ed.: H. A. Lieberman, L. Lachman, J. B. Schwartz is a good example. It also mentions (page 187) additional methods: Electronic sensing zone, light obstruction, air permeation, sedimentation in gas or liquid. However, the values of the particle size distributions used in the present invention are generally obtained by the Laser diffraction analytical technologies (see for example http://pharmazie-lehrbuch.de/kapitel/3-1.pdf). More specifically the particle size distributions are obtained according to the invention with a LS 13 320 Laser Diffraction Particle Size Analyzer of Beckmann Coulter thereby relying in particular on the corresponding "LS 13 320 Laser Diffraction Particle Size Analyzer Instructions For Use PN B05577AB (October 2011)" using in particular the complete Mie theory. These laser diffraction analytical technologies yield volume weighted distributions. Here the contribution of each particle in the distribution relates to the volume of that particle (equivalent to mass if the density is uniform), i.e. the relative contribution will be proportional to size. More specifically the particle size distribution (PSD) in accordance with the present invention is carried out with a 20 g sample of the phosphate binder which is analyzed with a laser particle size analyzer Beckman Coulter LS equipped with a dry powder system. A run length of approx 13" and an obscuration of 4% is applied. The PSD is calculated from the cumulative percentage undersize size distribution using a computer program. Further details are shown in example 4 below.

Tablet thickness is measurable using a ruler, vernier caliper, a screw gauge or any electronic method to measure dimensions. Such methods are well known and described in the art such as in any analytical chemistry text book or by the United State Pharmacopeia's (USP) publication USP-NF (2004) which describes the US Food and Drug Administration (FDA) enforceable standards.

This invention provides in particular a compressed tablet or direct compressed tablet, especially chewable tablet, which is capable of disintegrating in water within a period of less than 30 minutes, or preferably between 5 to 25 minutes to provide a dispersion which is capable of passing through a sieve screen with a mesh aperture of 710 μm in accordance with the herein defined British Pharmacopoeia test for dispersible tablets.

Preferably the disintegrating time of a tablet according to the invention is less than 20 minutes, more preferably less than 18 minutes and most preferably less than 20 minutes, still more preferably 12 to 20 minutes.

Furthermore the disintegrating times and relatively fine dispersions obtained with tablets according to the invention are also advantageous regarding the phosphate absorption capabilities. Thus tablets according to the invention can be presented for disintegrating in water or in the oral cavity as chewable tablets and also for directly swallowing. Those tablets according to the invention that are intended to be swallowed are preferably film-coated to ease application.

The present invention also concerns the use of particles comprising a phosphate binder, especially particles comprising sucroferric oxyhydroxide for the preparation of a of a pharmaceutical composition, in particular a compressed or a directly compressed tablet, wherein at least 40%, preferably 60%, most preferably 80% even more preferably 90% (by volume), of the particles, especially of the sucroferric oxyhydroxide particles in the a particle size distribution are between 4 to 200 μm or preferably between 5 to 160 μm or in between 21 to 160 μm.

The present invention also concerns the use of particles comprising a phosphate binder, especially particles comprising sucroferric oxyhydroxide for the preparation of a compressed or a directly compressed tablet, wherein the phosphate binder has a d50 in the particle size distribution of between 40 μm to 80 μm or between 42 μm to 75 μm.

The present invention also concerns the use of particles comprising a phosphate binder, especially sucroferric oxyhydroxide for the preparation of a pharmaceutical composition or a compressed or a directly compressed tablet, wherein;
  i) the phosphate binder has a d50 in the particle size distribution of between 30 μm to 120 μm, or 35 μm to 110 μm, or 40 μm to 108 μm, or 40 μm to 100 μm, or preferably of between 40 μm to 80 μm or between 42 μm to 75 μm, and/or
  ii) at least 40%, preferably 60%, most preferably 80% even more preferably 90% (by volume), of the sucroferric oxyhydroxide particles have a particle size in the particle size distribution of between 4 to 200 μm or preferably between 5 to 160 μm or between 21 to 160 μm.

In a further preferred embodiment, the pharmaceutical composition is in the form of a powder or of granules which can further be mixed with at least one pharmaceutically acceptable excipient, most preferably in the form of a powder if the pharmaceutical formulation is directly compressed into a tablet or used for granulation.

In a preferred embodiment, the used pharmaceutical formulation preferably contains a lubricant, which is preferably magnesium stearate.

In addition to the active ingredient (phosphate binder particles), the pharmaceutical compositions (e.g. tableting powders or tableting granules) may contain a number of inert materials known as excipients (or pharmaceutically acceptable excipients). They may be classified according to the role they play in the final tablet. Excipients are selected to aid in the processing and to improve the properties of the final product, and may be classified according to the role they play in the final tablet. They may include fillers, binders or diluents, lubricants, disintegrants and glidants. Other excipients which contribute to the physical characteristics of the finished tablet are e.g. coloring agents, and flavors in the case of chewable tablets. Typically, excipients are added to a formulation to impart good flow and compression characteristics to the material being compressed. Such excipients and corresponding ranges are particularly described in the International Patent application WO2009/06993 A1. Typically not more than 35% (by weight on a dry weight basis) of excipients are added to the total of the pharmaceutical composition.

In a preferred embodiment, this invention concerns any of the herein described pharmaceutical compositions, or compressed tablets preferably direct compressed pharmaceutical tablets, wherein at least one of the pharmaceutically acceptable excipients is used in an amount of for example 0.01% to 10% or 0.01% to 6% or 0.1% to 6% (by weight on a dry weight basis). In the most preferred embodiment of using sucroferric oxyhydroxide as the phosphate binder particles (consisting essentially (i.e. except impurities, i.e. generally more than 95 or 98 wt-%) of iron(III)-oxyhydroxide stabilized by sucrose, and starches) as an additional excipient only those selected from flavor, sweeteners or taste-enhancing agents, glidants or lubricants, the latter being preferably selected from magnesium stearate or colloidal silicas like Aerosil®, are used in an amount of at most 10%, preferably at most 6%, more preferably at most 3% (by weight on a dry weight basis).

In a preferred embodiment, this invention concerns any of the herein described pharmaceutical compositions, or compressed tablets preferably direct compressed pharmaceutical tablets, wherein at least one the pharmaceutically acceptable excipient is a lubricant preferably magnesium stearate and a flavor agent.

One, two, three or more diluents or fillers can be selected as further pharmaceutically acceptable excipient. Examples of pharmaceutically acceptable fillers and pharmaceutically acceptable diluents include, but are not limited to, e.g. confectioner's sugar, compressible sugar, dextran, dextrin, dextrose, lactose, mannitol, microcrystalline cellulose, powdered cellulose, sorbitol, sucrose and talc. The preferred diluents include e.g. microcrystalline cellulose. Microcrystalline cellulose is available from several suppliers. Suitable microcrystalline cellulose includes Avicel products, manufactured by FMC Corporation. Another diluent is e.g. lactose. The diluent, fillers, e.g., may be present in an amount from about 0.1% to 20% and about 0.5%-40% respectively by weight of the composition.

One, two, three or more disintegrants can be selected. Examples of pharmaceutically acceptable disintegrants include, but are not limited to, e.g. starches; clays; celluloses; alginates; gums; cross-linked polymers, e.g., cross-linked polyvinyl pyrrolidone, cross-linked calcium carboxymethylcellulose and cross-linked sodium carboxymethylcellulose; soy polysaccharides; and guar gum. The disintegrant, e.g., may be present in an amount from about 0.01% to about 10% by weight of the composition. A disintegrant is also an optional but useful component of the tablet formulation. Disintegrants are included to ensure that the tablet has an acceptable rate of disintegration. Typical disintegrants include starch derivatives and salts of carboxymethylcellulose. Sodium starch glycolate is the preferred disintegrant for this formulation.

One, two, three or more lubricants can be selected. Examples of pharmaceutically acceptable lubricants and pharmaceutically acceptable glidants include, but are not limited to, e.g. colloidal silica, magnesium trisilicate, talc, tribasic calcium phosphate, magnesium stearate, aluminum stearate, calcium stearate, stearic acid, polyethylene glycol and glycerol behenate. The lubricant, e.g., may be present in an amount from about 0.01 to 10% or from 0.1% to about 6% by weight of the composition; whereas, the glidant, e.g., may be present in an amount from about 0.01 to 10% or about from 0.1% to about 10% by weight. Lubricants are typically added to prevent the tablet blend from sticking to punches, minimize friction during tablet compression and allow for removal of the compressed tablet from the die. Such lubricants are commonly included in the final tablet mix in amounts usually around or less than 2% by weight. The lubricant component may be hydrophobic or hydrophilic. Examples of such lubricants include e.g. stearic acid, talc and magnesium stearate. Magnesium stearate reduces the friction between the die wall and tablet mix during the compression and ejection of the tablets. It helps prevent adhesion of tablets to the punches and dies. Magnesium stearate also aids in the flow of the powder in the hopper and into the die. The preferred lubricant, magnesium stearate is also employed in the formulation. Preferably, the lubricant is present in the tablet formulation in an amount of from about 0.01 to 10% or from about 0.1% to about 6%; also preferred is a level of about 0.1% to about 4% by weight; and most preferably from about 0.1% to about 2% by weight of the composition. Other possible lubricants include talc, polyethylene glycol, silica and hardened vegetable oils. In an optional embodiment of the invention, the lubricant is not present in the formulation, but is sprayed onto the dies or the punches rather than being added directly to the formulation.

In addition, tablets often contain diluents or fillers which are added to increase the bulk weight of the blend resulting in a practical size for compression (often when the dose of the drug is smaller).

Conventional solid fillers or carriers are substances such as, e.g. cornstarch, calcium phosphate, calcium sulfate, calcium stearate, glyceryl mono- and distearate, sorbitol, mannitol, gelatin, natural or synthetic gums, such as carboxymethyl cellulose, methyl cellulose, alginate, dextran, acacia gum, karaya gum, locust bean gum, tragacanth and the like, diluents, binders, disintegrating agent, coloring and flavoring agents could optionally be employed.

Binders are agents, which impart cohesive qualities to the powdered material. Examples of pharmaceutically acceptable binders as excipients include, but are not limited to, starches, sugars; celluloses and derivatives thereof, e.g., microcrystalline cellulose, hydroxypropyl cellulose, hydroxylethyl cellulose and hydroxylpropylmethyl cellulose; sucrose; glucose, dextrose, lactose dextrose; corn syrup; polysaccharides; and gelatin. During the clinical trials, the applicant has furthermore realized that the taste of the phosphate binder was not appreciated by the subjects and did directly affect the compliance with the therapeutic treatment (treatment adherence). For sake of clarity it should be noted that sucrose and starches being part of the active ingredient sucroferric oxyhydroxide or PA21 do not count as excipients, like binders, sweeteners, etc. listed here.

In further embodiment the formulations, compositions and tablets of the invention comprise one or more flavoring or taste-masking and coloring additives such as e.g., flavours, sweeteners, taste-enhancing agents, colorants, and the like, which are typically used for oral dosage forms.

In preferred embodiment the formulations, compositions and tablets of the invention comprise a flavouring agent with Woodberry flavour. The Woodberry flavor provides better compliance and acceptance of the claimed phosphate binder tablets.

Taste-masking agents, such as a taste-enhancing agent, flavouring agent, and/or natural or artificial sweetener, including intense sweetener, are incorporated into oral dosage forms, such as chewable dosage forms, to give them a more pleasant taste or to mask an unpleasant one.

Typical sweeteners as excipient include, but are not limited to, sugars like e.g. sucrose, fructose, lactose, confectionery sugar, powdered sugar, or are polyols which is e.g. sorbitol (e.g. Neosorb), xyitol, maltitol, maltose and polydextrose, or a mixture thereof. Typical intense sweeteners may include, but not be limited to, e.g. aspartame, sucralose, acesulfame K, and/or saccharin derivatives, or a mixture thereof. Further suitable sweeteners or taste-enhancing agents include glycosides such as e.g. neohesperidin dihydrochalcone (neohesperidin DC or NHDC), glycyrrhizin, glutamate, and the like. The latter may be used in very small quantities and thus may hereinafter also be called taste-enhancing agents. All the above are suitable to be used alone or as mixtures with other sweeteners and/or flavouring agents. These substances insure great lingering of the sweet taste and cover any undesired aftertaste. Preferred sweeteners and/or taste-enhancing agents include glycosides such as neohesperidin dihydrochalcone.

In one embodiment the sweetener of choice may be present in an amount of 0.00001 to 2% (w/w), preferably 0.00001 to 0.1% (w/w), most preferably 0.00001 to 0.001% (w/w), in relation to the total weight of the composition.

The taste-enhancing agent of choice may be present in an amount of 0.1 to 50 ppm, preferably 1 to 10 ppm, most preferably 1 to 5 ppm, in relation to the total weight of the composition. Typical flavoring agents include any natural and artificial flavoring agent suitable for pharmaceutical applications, such as flavoring agents derived from a spice, fruit or fruit juice, vegetable or vegetable juice, and the like, for example flavors based on cocoa, caramel, vanilla, apple, apricot, berry (e.g. blackberry, red currant, black currant, strawberry, raspberry, Woodberry, etc.), mint, panettone, honey, nut, malt, cola, verveine (*Verbena*) or any combination thereof, such as for example caramel/vanilla, fruit/cream (e.g. strawberry/cream) and the like. In one embodiment the flavoring agent of choice may be present in an amount of 0.01 to 12% (w/w), preferably 0.1 to 6% (w/w), most preferably 0.1 to 4% (w/w), in relation to the total weight of the composition.

Additional examples of useful excipients are described in the Handbook of pharmaceutical excipients, 3rd edition, Edited by A. H. Kibbe, Published by: American Pharmaceutical Association, Washington D.C., ISBN: 0-917330-96-X, or Handbook of Pharmaceutical Excipients (4$^{th}$ edition), Edited by Raymond C Rowe-Publisher Science and Practice which are incorporated herewith by reference.

The above described formulations are particularly adapted for the production of pharmaceutical compositions e.g. tablets, compressed tablets or preferably direct compressed tablets, caplets or capsules and provide the necessary physical characteristics, regarding e.g. dissolution and drug release profiles as required by state of the art dosage forms in the field. Therefore in an additional embodiment, the present invention concerns the use of any of the above described pharmaceutical compositions, tablets, chewable tablet, granules, caplets or capsules in particular for granulation, direct compression and dry granulation (slugging or roller compaction).

The above compositions are also particularly useful for the production of tablets especially compressed tablets and very preferably direct compressed tablets e.g. chewable tablets.

The tablets obtained with the above described compositions especially when processed in the form of direct compressed tablets or the herein described direct compressed tablets, exhibit preferable friability properties very good breaking strength, improved manufacturing robustness, optimal hygroscopicity, hardness, compressibility, chewability, low residual water content especially for direct compressed tablets, short Disintegration time DT (less than 30 minutes) according to the British Pharmacopoeia 1988, resulting in a fine dispersion with a preferable particle size distribution after disintegration. Although, the Disintegration time DT values claimed in the present application have been obtained according to the European Pharmacopoeia (EP) 04/2011: 20901 defined methodologies.

Preferably the hereinabove described compressed tablets (e.g. direct compressed tablets), have a disintegration time less than 30 minutes, preferably between 5 and 20 minutes.

Preferably for the hereinabove described compressed tablets (including direct compressed tablets) have a tablet hardness of comprised between 70 N to 250 N or between 80 to 200 N, preferably between 100 N to 230 N, and a friability of between 0% to 7% or 0.5 to 7%.

This present invention of direct compression of phosphate binders especially sucroferric oxyhydroxide involves blending and compression. The choice of grades of excipients added in particular to the claimed sucroferric oxyhydroxide particles, takes the particle size range of the sucroferric oxyhydroxide particles into consideration to be maintained within a range that allows homogeneity of the powder mix and content uniformity of the phosphate binder particles especially sucroferric oxyhydroxide particles in the final dosage form, and as explained before the particle size distribution of the selected further excipients comprised in the pharmaceutical formulation or a pharmaceutical composition or tablets is preferably similar to the particle size distribution of the phosphate binder particles preferably the sucroferric oxyhydroxide particles. This prevents segregation of the particles in the hopper during direct compression. The advantages of using the claimed pharmaceutical compositions are that they impart compressibility, cohesiveness (reducing it) and flowability (increasing it) of the powder blend. In addition, the use of direct compression provides competitive unit production cost, shelf life, eliminates heat and moisture, allows for prime particle dissociation, physical stability and ensures particle size uniformity.

The described advantages of the claimed pharmaceutical compositions are also very useful for e.g. roller compaction or wet granulation or to fill sachets or capsules.

In a further embodiment, the herein described and claimed pharmaceutical compositions and tablets (e.g. direct compressed tablets) contain one or more further phosphate binder preferably one or two further phosphate binders.

Preferred further phosphate binders are especially organic polymers such as e.g. sevelamer hydrochloride. Management of the phosphorus level is one of the primary treatments for CKD-MBD using phosphate binders to reduce the serum phosphate concentration. Sevelamer is marketed under the brand name Renagel® (hydrochloric acid) and Renvela® (Carbonate formulation) by Genzyme.

Other Phosphate binders that may be used include in particular calcium, magnesium, aluminum, iron, lanthanum and bismuth salts, whose which are better soluble than the corresponding phosphate salts of these cations. In addition, phosphate-binding organic polymers having an anion exchanger function such as AMG 223 (Amgen) and MCI-196 (Colestilan, Mitsubishi) are suitable substances for the invention. Suitable aluminum salts include all the pharmaceutically tolerable salts which fulfill the above requirements, especially oxides, in particular algedrate and/or hydroxides. All the pharmaceutically acceptable salts which fulfill the above requirements, in particular lanthanum carbonate including its hydrates are suitable as the lanthanum salts. All the pharmaceutically acceptable salts which fulfill the above requirements, preferably chlorides, sulfates, hydroxides, oxides, carbonates and in particular heavy magnesium carbonate are suitable as the magnesium salts. Preferred phosphate binders based on metal salts are for example, fermagates and calcium salts, preferably calcium carbonate and/or calcium chloride and especially preferably calcium acetate.

The present invention also covers any of the herein above claimed pharmaceutical compositions or tablets comprising a second phosphate binder selected from e.g. any of Sevelamer hydrochloric acid formulation (Renagel®), Sevelamer Carbonate formulation (Renvela®), calcium, magnesium, aluminum, iron, lanthanum salts and bismuth salts.

EXPERIMENTAL SECTION

Example 1

The tablets prepared as herein above described can be tested as follows.
Tablet Evaluation Methods
1. Average tablet weight. Twenty tablets are weighed on an analytical balance and the average tablet weight calculated.
2. Tablet breaking strength N. 5 tablets are individually tested using a Schleuniger crushing strength tester, and the average breaking strength calculated.
3. Friability (% loss). 10 tablets, accurately weighed, are subjected to 10 minutes friability testing using a Roche Friabilator (as described and measured under the conditions of example 4(C)). The tablets are dedusted, reweighed, and the weight loss due to the friability is calculated as a percentage of the initial weight. The friability data and values claimed in the present application have been measured according to the European Pharmacopeia's 01/2010: 20907 with a Roche friabilator.
4. Disintegration time DT (as defined in the European Pharmacopoeia 04/2011:20901). 6 tablets are tested in accordance to the above-defined EP test.
5. Dispersion Quality. In accordance with the BP uniformity of dispersion test for dispersible tablets (BP 1988 Volume II page 895), two tablets are placed in 100 ml of water at 19-21° C. and allowed to disperse.
Granule Evaluation Methods
1. Loss on Drying (LOD). The residual moisture content of the granule (LOD) can be determined on a 3-4 g sample using a Mettler moisture analyser set at 105° C. for 10 min. operated in accordance with the manufacturer's procedure.
2. Particle size distribution (PSD). A 20 g sample of sucroferric oxyhydroxide as the phosphate binder is analyzed with a laser particle size analyzer Beckman Coulter LS 13 320 equipped with a dry powder system, thereby relying in particular on the corresponding "LS 13 320 Laser Diffraction Particle Size Analyzer Instructions For Use PN B05577AB (October 2011)" using in particular the complete Mie theory. These laser diffraction analytical technologies yield volume weighted distributions (see e.g. FIG. 2). A run length of approx 13" and an obscuration of 4% is applied. The PSD is calculated from the cumulative volume percentage undersize size distribution using a computer program.

Example 2: Improved Manufacturing Robustness

A preliminary compactibility assessment is carried out on a Kilian press using different formulations of sucroferric oxyhydroxide with different excipients e.g. magnesium stearate.

Data demonstrate that our claimed pharmaceutical compositions on being compressed with increasing levels of pressure (compression force) show a substantially useful increase in tablet strength. In particular e.g. mixture of sucroferric oxyhydroxide with magnesium stearate show a substantially useful increase in tablet strength if sucroferric oxyhydroxide is within the hereinabove claimed particle size distribution. These results indicated that from compressibility point of view the claimed formulations provide a clear improvement. With increasing pressure (compression force) our claimed formulations show a substantially useful increase in tablet strength.

A compressibility study is carried out on an instrumented Fette 102i press with force and displacement sensors on both upper and lower punches.

A clear indication is afforded from these data that sucroferric oxyhydroxide tablets are very likely to have poor tablet hardness/crushing strength unless proper particle size are selected. Our claimed formulations are particularly adapted to provide the required compactibility.

Example 3: Friability

Evaluation can alternatively be carried out using a Fette 2200 press at 6 different settings: strain rate settings of 30,000 to 70,000 tablet per hour) and main compression force of 35-55 kN. The trials use Flat-faced Beveled-edge (FFBE) tooling of 20 mm diameter for 2577.5 mg tablets (other diameters are used depending on the weight of the tested tablet). The friability data and values claimed in the present application have been measured according to the European Pharmacopeia's 2.9.7 with a Roche friabilator. Total tablet weights were selected so that both the 20 mm FFBE tablets would have 2500 mg of sucroferric oxyhydroxide and identical tablet thickness. Friability, Compression profile, Strain rate profile and Weight variation are the measured outcomes. Study design and the friability results obtained from the study are used to determine the variables (particle size distribution in the formulation, tablet weight, tablet thickness and weight, water content in the tablet etc) impacting the outcome of hardness.

Example 4: Particle Size Distribution Measured by Laser Diffraction

The sucroferric oxyhydroxide particle size distribution having particles in the range of 1 to 200 μm or 4 to 200 μm or 5 to 160 μm or between 21 to 160 μm, or with a d50 in the particle size distribution or between 30 μm to 120 μm, or 35 μm to 110 μm, or 40 μm to 100 μm, or preferably of between 40 μm to 80 μm or between 42 μm to 75 μm, and which is particularly adapted to produce the herein described formulations especially the direct compressed tablets, can be produced as described below.

The methods and values describe in the below example 4, are the basis supporting the values included in the present claims.
1. Preparation of Particle Size Distribution via a sucroferric oxyhydroxide applied for Direct Compression Tablets.

The applicant has discovered a particle size distribution (e.g. having particles mainly (e.g. more than 50 volume-%)

between 10 to 152 μm) of in particular sucroferric oxyhydroxide (or with a d50 of the particle size distribution of between 40 μm to 80 μm or preferably between 42 μm to 75 μm), which is particularly suitable for direct compression tablets of phosphate binders.

Improved results are obtained with a d50 of the particle size distribution of between 30 μm to 120 μm, or 35 μm to 110 μm, or 40 μm to 108 μm, or 40 μm to 100 μm, or preferably between 40 μm to 80 μm or preferably between 42 μm to 75 μm.

The particle size distribution determined by laser light diffraction method is preferably specified as follows: d10 larger or equal 5 μm, d50 larger or equal 35 μm, preferably between 40 μm to 80 μm or between 42 μm to 75 μm and d90 less or equal 380 μm. Particle size have been measured by laser diffraction.

Equipment:

Measuring device: e.g. LS 13 320 Laser Diffraction Particle Size Analyzer of Beckmann Coulter, Beckman Coulter International S.A. Switzerland Sample module: Vacuum pressure dispersion system, e.g. Dry Powder System (Tornado), Beckman Coulter International S.A. Switzerland Conditions:

Average vacuum: 25-30" $H_2O$; Obscuration approx. 48-10%; Run length approx. 25 seconds'.

Procedure:

Introduce 20 g of the sample into the Dry Powder dispersion System.

Measurement: Apply the specified vacuum to transfer the sample and determine the cumulative volume distribution using a laser light diffraction instrument in accordance with the instruction manual. The parameters may be adjusted so that the test dispersion is representative, homogeneous and well dispersed.

Evaluation/assessment: Determine the particle sizes at the undersize values of 10%, 50% and 90% (d10, d50, d90), and additional values in question, from the cumulative volume distribution.

The inventive particle size distribution (in particular the sucroferric oxyhydroxide particle size distribution) can be obtained by the below described process, which is a nonelimiting example. Alternative processes can easily be implemented by the person skied in the art.

A. Manufacturing Process.

The sucroferric oxyhydroxide drug substance is basically prepared as described in the European Patent WO9722266A1 or in the patent application WO2008/062993.

The manufacturing process for the sucroferric oxyhydroxide drug substance (named PA21 in the below FIG. 1) yields a stabilized polynuclear β-iron(III)-oxyhydroxide with a particularly high phosphate adsorption capacity that is maintained dung long-term storage.

A flow chart of the manufacturing process is provided in below. It comprises the following steps:

Synthesis of iron(III)-oxyhydroxide by precipitation of an iron salt (e.g. iron(III)-chloride) with a base (sodium carbonate which was found to be the best choice). The process was optimised by keeping the addition of iron(III)-chloride and the stirring rate adjusted.

Desalination: Excess sodium chloride formed is removed by means of a washing step with water.

Addition of starches and sucrose to the iron(III)-oxyhydroxide suspension in a relative mass ratio of starch to sucrose to iron of preferably 1.5:1.5:1 under constant stirring. This step is performed in order to stabilise the iron(III)-oxyhydroxide and to allow further processing.

Spray drying under controlled conditions as described above.

The resulting sucroferric oxyhydroxide drug substance can be obtained with the desired particle size distribution by adapting the spray drying settings as described above in particular using a centrifugal atomization unit. By spray drying, the different settings of the atomizer in the spray dryer are selected to obtain the desired particle size distribution. This technique is known by the person skilled in the art and settings can depend on the used spray dryer equipment and suitably adapted. Optionally, the obtained resulting sucroferric oxyhydroxide drug substance can be further processed to obtain the desired particle size distribution by other well-known techniques such as by mechanical stress.

FIG. 2 shows the Particle Size Distribution of the obtained PA21 Drug Substance resulting from spray drying process and analyzed using a LS 13 320 Laser Diffraction Particle Size Analyzer of Beckmann Coulter.

B. Mechanical Stress

Basically the phosphate absorber particles in the desired particle size range can be also obtained by mechanical stress. This stress can be mediated by impact, shear or compression. In most commercially available grinding equipment a combination of these principles occurs. For the sucroferric oxyhydroxide obtained by the above described manufacturing process preferably a mechanical impact or jet mill might be used apart from the preferred spray drying process. The most preferable mechanical impact mill can be equipped with different kind of beaters, screens, liners or with pin plates. For our process an impact mill with plate beater and a slit screen 5*2.5 cm is used. The impact speed should be variable between 20 and 100 m/s (as peripheral speed) to adapt to any batch to batch variation. A peripheral speed of the beater of about 40-50 m/s is used.

Good results (particle size distribution) can also be obtained by mechanical stress e.g. roller compaction, milling and/or sieving.

Other techniques as described in the art and commonly used by the person skilled in the art can also be used to obtain targeted particle size range.

In order to evaluate the compressibility of API (Active Pharmaceutical Ingredient: sucroferric oxyhydroxide) batch with different particle size distribution different API batch covering the range from approximately 40 μm to 110 μm were selected.

Characteristics of the Selected Sucroferric Oxyhydroxide API Batches:

|  | Batch number | | | |
| --- | --- | --- | --- | --- |
|  | 030609-02 | 070609-01 | 090609-01 | 110709-01 |
| Iron content [%] | 20.95 | 20.66 | 20.53 | 22.08 |
| LOD [% m/m] | 6.07 | 6.07 | 6.46 | 5.34 |
| Particle size distribution [μm] | | | | |
| d10 | 25.29 | 17.69 | 16.76 | 10.64 |
| d50 | 109.3 | 65.53 | 75.10 | 42.85 |
| d90 | 207.2 | 135 | 151.6 | 96.89 |
| Bulk density [g/ml] | 0.85 | 0.85 | 0.834 | 0.894 |
| Tapped density [g/ml/] | 1.013 | 1.013 | 0.963 | 1.011 |
| Hausner factor | 1.1919 | 1.1919 | 1.1538 | 1.1313 |
| Respose angle | 20.25° | 20.25° | 18.68° | 21.33° |
| Powder flow [g/s] | 32.95 | 32.95 | 34.08 | 27.86 |

All API batch presented similar flowability, density and LOD. The variability of iron content was in the usual range for this kind of product. The major difference was only the particle size distribution.

C. Tablet Compression

Equipment:

Tabletting press: Rotative Killian E 150 equipped with 20 mm flat faced punches

Tablet hardness: 5 tablets are individually tested using a Schleuniger crushing strength tester, and the average breaking strength calculated. The tablet hardness is measured according to the European Pharmacopoeia 01/2008:20908.

Tablet thickness: 5 tablets are individually measured with a caliper and the average thickness is calculated Tablet friability: friability is measured according to the European Pharmacopeia's 01/2010:20907 with a Roche friabilator Mean mass: 10 tablet are weighted and the mean mass is calculated Disintegration (as defined in the European Pharmacopoeia 04/2011:20901) are carried out with standard equipment (Sotax DT3 disintegration tester) on 6 tablets 1. Preparation of the Pharmaceutical Formulation Powders.

The different API batches (with the different particle size ranges) were all formulated with the following composition (pharmaceutical formulation) in the form of a powder comprising the sucroferric oxyhydroxide particles:

| Component | Function | [mg] |
|---|---|---|
| Composition per tablet: | | |
| PA21-2 powder[1] | Active ingredient | 2,500.00 |
| corresponding to iron | | 500.00 |
| Woodberry flavour | Flavour | 40.00 |
| Neohesperidin dihydrochalcone | Sweetener | 0.01 |
| Magnesium stearate | Lubricant | 25.00 |
| Silica (colloidal, anhydrous) | Flow aid | 12.49 |
| Total | N/A | 2,577.50 |

[1]Iron(III)-oxyhydroxide, sucrose, potato starch, pregelatinised starch (sucroferric oxyhydroxide).

2. Preparation of the Compressed Tablets.

Following equipment were used for the preparation of the blend:

Tumbling blender (Röhnrad Engelsmann), Quadro comill 193

Magnesium stearate, silica and neohesperidin DHC were purchased of PhEur quality. The selected flavours are standard flavours used for food and pharmaceutical product.

An identical manufacturing process by direct compression was applied to all API batch to compare their processability. The manufacturing process consisted of:

Sieving and blending of all ingredients

Lubrication by the addition of magnesium stearate

Tabletting into biplanar tablets with 20 mm diameter on a rotating tablet press

The tablet weight was adjusted according to the drug substance assay to provide a nominal dosage of 500 mg iron i.e. 2500 mg of sucroferric oxyhydroxide.

Tabletting trials were performed in order to optimize the hardness of the tablet. For such a 20 mm tablet a hardness of at least 100 N is necessary to able filling of the tablet in standard packaging without break of damage of the tablet.

Following tableting trials were done:

| | Tabeletting trials | | | | | |
|---|---|---|---|---|---|---|
| | E222X380 | E222X381 | E222X382 | E222X382B | E222X383 | E222X383B |
| Batch Nr API | 070609-01 | 030609-02 | 090609-01 | 090609-01 | 110709-01 | 110709-01 |
| Hardness [N] | 106 | 83 | 93 | 121 | 88 | 140 |
| Mean mass [mg] | 2588 | 2536 | 2570 | 2575 | 2542 | 2525 |
| Thickness [mm] | 6.31 | 5.89 | 6.39 | 6.26 | 6.24 | 6.10 |
| Friability [%] | 6.87 | 10.82 | 6.84 | 4.05 | 6.53 | 3.50 |
| Disintegration [%] | 9.23 | 19.51 | 8.81 | 13.52 | 6.28 | 9.18 |

Based on the knowledge in the art, for a big tablets like the developed high load direct compressed tablets (i.e. 2500 mg of sucroferric oxyhydroxide), the ideal d50 should have been between 200 to 350 μm. Nobody would have expected that the claimed small sucroferric oxyhydroxide particle size could have resulted in improved tablet (direct compressed high load tablets) i.e. improved physical properties.

Surprisingly the sucroferric oxyhydroxide particles, with a d50 of 109 μm (batch no. 030609-02) could not yield in tablet with the most favorable targeted hardness while still acceptable. A maximum of 83 N was reached on the tablet press at this point the compression force was already maximal and the noisy sound of the machine oblige us to stop the experiment to not damage the press. Although the tablet was compressed at the lowest thickness we obtained the lowest hardness. The tabletting trials E222X383B with a d50 of 43 μm and E222X382B with a d50 of 75 μm allowed surprisingly to increase the compression force resulting into the increase of the hardness, which was not the case with e.g. batches with a d50 of 109 μm. With such batches (d50 of >109 μm) whatever the used compression force is, it was not possible to obtain tablets with improved hardness. Therefore a d50 of around 109 μm is a upper limit zone of what is still acceptable. So a reasonable upper limit is in the zone of 110 or 120 μm. At 120 μm, the hardness shall be around 80 N or slightly lower than 80 N.

Trials performed with sucroferric oxyhydroxide particles with a d50 in the range of 42 to 75 μm revealed a surprisingly good compressibility of the material and allowed to target up to 140 N of hardness.

Sucroferric oxyhydroxide particles with a d50 less than around 42 μm were considered as less appropriate for tableting as they would result in too much loss of material in a rotating tableting machine.

Based on the experimental evaluations, the hereinabove claimed improvements are observed with sucroferric oxyhydroxide particles having a d50 between 30 μm and 120 μm or a d50 between 35 μm and 110 μm. The best results are observed with sucroferric oxyhydroxide (API) particles having a d50 between 40 μm to 108 μm, 40 μm and 100 μm or preferably between 40 μm and 80 μm.

FIG. 3 demonstrates that the sucroferric oxyhydroxide (API) particles with a d50 between 40 and 80 μm is particularly preferred to get a minimum of 100 N.

The disintegration time obtained with the sucroferric oxyhydroxide particles with a d50 of 109 µm (batch 030609-02) for tablet of 83 N was 300% higher (19'51") than tablet of similar hardness (88N) obtained with an API with a d50 of 42 µm (110709-01) that disintegrate in 6'28". Such difference could impact the dissolution time of the tablet and is less favourable.

To confirm the excellent compressibility of the sucroferric oxyhydroxide particles the compression profile has been investigate on an additional batch with a d50 of 50.3 µm The tablet batch 1260111 has been produced on a rotating tableting machine gave following results:

| Tablet thickness [mm] | 6.22 | 6 | 6.04 | 5.85 | 5.82 |
|---|---|---|---|---|---|
| Hardness [N] | 78 | 113 | 132 | 154 | 187 |
| Compression force [kN] | 37 | 40 | 45.6 | 48.7 | 50.6 |
| Friability [%] (with abrasion wheel) | 1.2 | 0.4 | 0.1 | 0.1 | 0.2 |

As shown in FIG. 4 the sucroferric oxyhydroxide particles with a d50 of 50 µm showed very good compression properties and show a linear increase of the hardness in function of the force. Tablet up to 187 N could be manufactured.

Example 5: Alternative Studies to Test the Chewability of the Compressed Chewable Tablets of the Invention The pharmacopoeia tests of (diametrical or radial) hardness (resistance to crushing Ph. Eur. 2.9.8), friability (Ph. Eur. 2.9.7) and disintegration (Ph. Eur. 2.9.1) are carried out with standard equipment (Erweka TBH 220 hardness tester, Erweka TA 120 friability tester with standard drum and abrasion drum (or Roche friabilator), and Sotax DT3 disintegration tester). To avoid any confusion, it is emphasized that the friability values claimed in the present application have been measured according to the European Pharmacopeia's 01/2010:20907 with a Roche friabilator, that the disintegration values claimed in the present application have been measured according to the European 04/2011:20901 are carried out with standard equipment (Sotax DT3 disintegration tester), and the tablet hardness values claimed in the present application have been measured using a Schleuniger crushing strength tester, i.e. conditions as described in example 4 according to the European Pharmacopeia's 01/2008:20908.

In addition, axial hardness (ring and tube test), grinding properties (plate test) are also measured using the texture analyzer (TAXt2i® Texture Analyser Stabel Micro Systems Ltd, Godalming, UK), used to measure the texture of a wide variety of materials. In addition, the Kramer shear cell, from Instron High Wycombe, UK ( ), used in the food industry to provide information on bite characteristics, crispness and firmness, and a Typodont D85SDP-200 Model from Kilgore International Inc., Coldwater, Mich., USA ( ) are also used in this study to test the chewability of tablets. The load was applied to the Typodont Model by the texture analyzer, which means that the Typodont model is an accessory to the texture analyzer in the tests carried out here.

The following test is carried out with both dry and artificial saliva wetted tablets.

The artificial saliva was prepared according to the modified recipe of Klimek (1982) (Original: Matzker and Schreiber (1972)):

| Ascorbic acid | 0.002 g/l |
|---|---|
| Glucose | 0.030 g/l |
| NaCl | 0.580 g/l |
| $CaCl_2$ | 0.170 g/l |
| $NH_4Cl$ | 0.160 g/l |
| KCl | 1.270 g/l |
| NaSCN | 0.160 g/l |
| $KH_2PO_4$ | 0.330 g/l |
| Urea | 0.200 g/l |
| $Na_2HPO_4$ | 0.340 g/l |
| Mucine | 2.700 g/l |

The prepared solution (500 ml) was kept refrigerated (4-6° C.) because of its limited shelf life.

Ring Test

In this test, the plastic tool simulates teeth being loaded onto a tablet, with the ring simulating the lower mandible. The ring test is close to an actual biting event.

The ring external diameter $d_a$ is 20 mm. The inner diameter, and consequently the diameter of the central cavity $d_i$ is 14 mm, since the metal of the ring has a thickness of 3 mm. The plastic tool with rounded site of contact is a standard component of the texture analyser. The speed of descent of the plastic tool was 2 mm/sec. The distance travelled is set at 5 mm with a load cell of 50 KG and the texture operation mode is "return to start".

In addition, the ring test is essentially an axial breaking strength. The tablet rests on the ring. The force, $F_{max}$, where breakage occurs is noted. The energy exerted (area under the force-displacement curve, is calculated. The test is carried out on dry tablets and wet (wet by immersion by means of a tweezers in artificial saliva for 10 seconds).

Plate Test

The plate test measures the depth of penetration by the application of maximum force for repeated loadings, and thus simulates the effect of teeth penetration during repeated chewing actions.

Here, the tablet is placed on the grooved reverse side of the base plate of the texture analyzer and a force is repeatedly exerted on the tablet to simulate repeated chewing actions.

The texture analyzer test settings were "cycle until count mode", with a load intensity chosen which does not cause the tablet to break (35 N for a rate of descent of 0.2 mm/sec). The approaching rate (pre-test speed) was 0.5 mm/sec for increased sensitivity. The applied force at which the texture analyser should begin the actual measurement is set at 0.0493 N with what is called the trigger. A typical force-displacement curve for 10 cycles is shown. The plate test measures the depth of penetration by the application of maximum force for repeated loadings.

Other tests such as the Tube test, Kramer shear cell test or Typodont model test can be performed.

CONCLUSION

The texture tester in the ring test mode (yielding axial breaking strengths) is considered to best characterize the chewability features of the sucroferric oxyhydroxide direct compressed tablets of the present invention. The test confirms the chewability quality of the tablets of the invention.

A number of tests are evaluated in order to provide in vitro evidence of the chewability quality of a chewable tablet. The results are compared with those of two commercially available chewable tablets.

Of the tests which more closely mirror actual chewing action, the texture analyzer in the plate test mode was considered to be the most reliable, especially with tablets wetted with artificial *salvia* proved to be the most discriminatory and useful. Those sucroferric oxyhydroxide tablets produced within the target radial hardness of ca. 130 N performed well in this test and even the variant 141 (radial hardness 231.2 N) showed good chewable properties, confirming a shelf life limit of 230 N as suitable.

Sucroferric oxyhydroxide tablets within the target radial hardness limit exhibited chewability properties closely approaching those of the best non-phosphate binder product (Tablets A—Calcimagon®) and superior to best phosphate binder competitor (Tablets B—Fosrenol®) in these tests.

For patient compliance it is an advantage that the chewable tablets disintegrate if chewing for whatever reason is incomplete and that the tablet robustness is sufficient to allow proper handling and transport. Sucroferric oxyhydroxide tablets variants meet this requirement.

PREFERRED EMBODIMENTS OF THE INVENTION

The following summarizes particular preferred embodiments of the invention:

1. Embodiment

A compressed tablet, comprising the phosphate binder, said phosphate binder comprises particles having a particle size distribution with particles in the range of 4 to 200 μm. Preferably the phosphate binder consists of such particles.

2. Embodiment

A compressed tablet according to embodiment 1, comprising the phosphate binder, said phosphate binder comprises particles having a particle size distribution, wherein at least 40% of the particles have a particle size within the range of 4 to 200 μm.

3. Embodiment

A compressed tablet, comprising the phosphate binder, said phosphate binder comprises particles, having a particle size distribution, wherein d50 is in the range of 40 μm to 80 μm.

4. Embodiment

A compressed tablet according to any of the previous embodiments, wherein the phosphate binder comprises iron (III)-oxyhydroxide.

5. Embodiment

A compressed tablet according to any of the previous embodiments, wherein the phosphate binder comprises iron (III)-oxyhydroxide and at least one carbohydrate.

6. Embodiment

A compressed tablet according to any of the previous embodiments, wherein the phosphate binder comprises iron (III)-oxyhydroxide and sucrose.

7. Embodiment

A compressed tablet according to any of the previous embodiments, wherein the phosphate binder comprises iron (III)-oxyhydroxide, sucrose and at least one starch.

8. Embodiment

A compressed tablet according to any of the previous embodiments, which contains phosphate binder particles, especially of sucroferric oxyhydroxide, and at least one further pharmaceutically acceptable excipient, and wherein at least 40%, or at least 60%, or at least 80%, or at least 90% of the particles in the phosphate binder particle size distribution in the tablet are between 4 to 200 μm, or between 5 to 160 μm, or between 21 to 160 μm.

9. Embodiment

A compressed tablet, which comprises phosphate binder particles, especially of sucroferric oxyhydroxide and at least one further pharmaceutically acceptable excipient, and wherein the phosphate binder particles have a particle size distribution with a d50 between 30 μm to 120 μm, or 35 μm to 110 μm, or 40 μm to 100 μm, or preferably between 40 μm to 80 μm or between 42 μm to 75 μm.

10. Embodiment

A compressed tablet according to any of the previous embodiments, wherein the phosphate binder particles have a particle size distribution with a d50 between 30 μm to 120 μm, or 35 μm to 110 μm, or 40 μm to 100 μm, or preferably between 40 μm to 80 μm or between 42 μm to 75 μm.

11. Embodiment

A compressed tablet according to any of the previous embodiments, wherein the phosphate binder particles have a particle size distribution with a d50 between 40 μm to 80 μm and wherein at least 60%, or at least 80% of the particles of the phosphate binder particle size distribution in the tablet are between 4 to 200 μm or between 5 to 160 μm or in between 21 to 160 μm.

12. Embodiment

A compressed tablet, according to any of the previous embodiments, wherein: the phosphate binder particles have a particle size distribution with a d50 between 30 μm to 120 μm, or 35 μm to 110 μm, or 40 μm to 100 μm, or preferably between 40 μm to 80 μm or between 42 μm to 75 μm, and/or the hardness of the tablet is between 70 to 250 N, and/or the tablet friability is between 0% to 7% or between 0.05% to 7%, and/or the tablet has a disintegration time less than 30 min, or of between 5 to 20 min, and/or the tablet diameter is between 16 mm to 30 mm, the tablet weight is between 1500 mg to 3000 mg (preferably 2000 to 3000 mg) and the tablet thickness is between 4.5 mm and 7.5 mm.

13. Embodiment

A compressed tablet, according to any of the previous embodiments, wherein:
i) at least 40%, or at least 60%, or at least 80%, or at least 90% of the particles in the phosphate binder particle size distribution in the tablet are between 4 to 200 μm or between 5 to 160 μm or between 21 to 160 μm, and ii) the phosphate binder particles have a d50 in the particle size distribution between 30 μm to 120 μm, or 35 μm to 110 μm, or 40 μm to 100 μm, or preferably between 40 μm to 80 μm or between 42 μm to 75 μm, and iii) the hardness of the tablet is between 70 to 250 N, and iv) the tablet friability is between 0% to 7% or between 0.05% to 7%, and v) the tablet has a disintegration time of less than 30 min, preferably between 5 to 20 min, and vi) the tablet diameter is between 16 mm to 30 mm, the tablet weight is between 1500 mg to 3000 mg and the tablet thickness is between 4.5 mm to 7.5 mm.

14. Embodiment

A compressed tablet, according to any of the previous embodiments, wherein;
i) at least 60%, or at least 80%, or at least 90% of the particles in the phosphate binder particle size distribution in the tablet are between 5 to 160 μm, and
ii) the phosphate binder particles have a d50 in the particle size distribution between 30 μm to 120 μm, or 35 μm to 110 μm, or 40 μm to 100 μm, or preferably between 40 μm to 80 μm, and/or
iii) the hardness of the tablet is between 70 to 250 N, and/or
iv) the tablet friability is between 0% to 7% or between 0.05% to 7%, and/or
v) the tablet has a disintegration time of less than 30 min, preferably between 5 to 20 min, and/or
vi) the tablet diameter is between 16 mm to 30 mm, the tablet weight is between 1500 mg to 3000 mg (preferably 2000 to 3000 mg) and the tablet thickness is between 4.5 mm and 7.5 mm, and/or
vii) the tablet contains between 800 mg to 3000 mg of sucroferric oxyhydroxide.

15. Embodiment

A compressed tablet according to any of the previous embodiments, wherein:
viii) at least 80%, or at least 90% of the particles in the sucroferric oxyhydroxide particle size distribution are between 4 to 200 μm or in between 5 to 160 μm, and
ix) the sucroferric oxyhydroxide particles have a d50 in the particle size distribution between 30 μm to 120 μm, or 35 μm to 110 μm, or 40 μm to 100 μm, or preferably between 40 μm to 80 μm, and
x) the hardness of the tablet is between 70 to 250 N, and
xi) the tablet friability is between 0% to 7% or between 0.05% to 7%, and
xii) the tablet has a disintegration time of less than 30 min, or of between 5 to 20 min, and
xiii) the tablet diameter is between 16 mm to 30 mm and the tablet weight is between 1500 mg to 3000 mg or in between 2000 mg to 3000 mg and the tablet thickness is between 4.5 mm to 7.5 mm, and
xiv) the tablet contains between 1500 mg to 3000 mg of sucroferric oxyhydroxide.

16. Embodiment

A compressed tablet according to any of the any of the previous embodiments, which is a direct compressed pharmaceutical tablet.

17. Embodiment

A pharmaceutical formulation or a pharmaceutical composition, which contains phosphate binder particles comprising especially sucroferric oxyhydroxide and at least one further pharmaceutically acceptable excipient, and wherein the phosphate binder particles have a d50 in the particle size distribution of the phosphate binder particles between 40 to 105 μm, 40 to 100 μm, 40 μm to 80 μm or in between 42 μm to 75 μm.

18. Embodiment

A pharmaceutical formulation or a pharmaceutical composition, which contains phosphate binder particles comprising especially sucroferric oxyhydroxide and at least one further pharmaceutically acceptable excipient, and wherein at least 40%, or at least 60%, or at least 80%, or at least 90% of the phosphate binder particles in the particle size distribution are between 4 to 200 μm or between 5 to 160 μm or between 21 to 160 μm.

19. Embodiment

A pharmaceutical formulation or a pharmaceutical composition, according to embodiments 17 or 18, wherein at least 40%, or at least 60%, or at least 80%, or at least 90% of the phosphate binder particles in the particle size distribution are between 4 to 200 μm or between 5 to 160 μm or between 21 to 160 μm.

20. Embodiment

A tablet or pharmaceutical composition, according to any of the previous embodiments, wherein the phosphate binder particles especially the sucroferric oxyhydroxide phosphate binder particles, represent more than 65%, or more than 80%, or more than 90%, or more than 95% of the total weight of the tablet or of the pharmaceutical composition (by weight on a dry weight basis).

21. Embodiment

A tablet, a pharmaceutical formulation or a pharmaceutical composition, according to any of the previous embodiments, which comprises more than 65%, or more than 80%, or more than 90%, or more than 95%, or more than 98% of sucroferric oxyhydroxide particles, by weight on a dry weight basis.

22. Embodiment

A compressed tablet according to any of the previous embodiments, wherein;
xv) the phosphate binder is sucroferric oxyhydroxide,
xvi) at least 80%, or at least 90% of the sucroferric oxyhydroxide particles in the sucroferric oxyhydroxide particle size distribution are between 4 to 200 μm or between 5 to 160 μm,
xvii) the sucroferric oxyhydroxide particles have a d50 in the sucroferric oxyhydroxide particle size distribution between 30 μm to 120 μm, or 35 μm to 110 μm, or 40 μm to 100 μm, or preferably between 40 μm to 80 μm,
xviii) the tablet contains between 800 mg to 3500 mg or between 1500 to 3500 mg of sucroferric oxyhydroxide,

23. Embodiment xix) the sucroferric oxyhydroxide phosphate binder particles represent more than 80%, or more than 90% of the total weight of the tablet (by weight on a dry weight basis).

23. Embodiment

A compressed tablet according to any of the previous embodiments, which is a chewable tablet.

24. Embodiment

A compressed tablet according to any of the previous embodiments, wherein the hardness of the tablet is between 70 to 250 or between 85 to 250 N or between 70 to 200 N or between 85 to 200 N.

25. Embodiment

A tablet or a pharmaceutical composition according to any of the previous embodiments, wherein the single oral dosage form contains between 800 mg to 3500 mg of sucroferric oxyhydroxide, or between 1500 mg to 3500 mg of sucroferric oxyhydroxide, or between 1500 mg to 3000 mg of sucroferric oxyhydroxide.

26. Embodiment

A tablet or a pharmaceutical composition according to any of the previous embodiments, wherein the single oral dosage form contains between 800 mg to 3500 mg of sucroferric oxyhydroxide, or between 1500 mg to 3500 mg of sucroferric oxyhydroxide, or between 1500 mg to 3000 mg of sucroferric oxyhydroxide, and wherein at least 60%, or at least 80%, or at least 90% of the particles of the phosphate binder particle size distribution in the tablet are between 5 to 160 µm, and wherein the d50 of the phosphate binder particle size distribution is between 40 µm to 80 µm.

27. Embodiment

The use of particles comprising sucroferric oxyhydroxide for the preparation of a compressed or a directly compressed tablet, wherein:
xx) at least 40%, or at least 60%, or at least 80%, or at least 90% of the sucroferric oxyhydroxide particles in the particle size distribution are between 4 to 200 µm or preferably between 5 to 160 µm or between 21 to 160 µm, and/or
xxi) the sucroferric oxyhydroxide particles have a d50 in the particle size distribution between 30 µm to 120 µm, or 35 µm to 110 µm, or 40 µm to 100 µm, or preferably between 40 µm to 80 µm or in between 42 µm to 75 µm.

28. Embodiment

The use of sucroferric oxyhydroxide particles for the preparation of a pharmaceutical composition or a compressed or a directly compressed tablet, wherein:
xxii) the sucroferric oxyhydroxide particles have a d50 in the particle size distribution between 30 µm to 120 µm, or 35 µm to 110 µm, or 40 µm to 100 µm, or preferably between 40 µm to 80 µm or in between 42 µm to 75 µm, and/or
xxiii) at least 40%, or at least 60%, or at least 80%, or at least 90% of the sucroferric oxyhydroxide particles of the particle size distribution are between 4 to 200 µm or preferably between 5 to 160 µm or between 21 to 160 µm.

29. Embodiment

Use of the sucroferric oxyhydroxide particles according to embodiment 27 or 28, wherein the sucroferric oxyhydroxide represents more than 80% or more than 90%, or more than 95% of the sucroferric oxyhydroxide particles, by weight on a dry weight basis of the pharmaceutical composition or the compressed tablet.

30. Embodiment

A pharmaceutical formulation according to any of the previous embodiments, which is in the form of a powder or of granules which can further be mixed with at least one pharmaceutically acceptable excipient.

31. Embodiment

A pharmaceutical formulation according to embodiment 30, in the form of a powder to be directly compressed into a tablet or used for granulation.

32. Embodiment

A pharmaceutical formulation, pharmaceutical composition, or a compressed tablet according to any of the previous embodiments, which comprises at least one further pharmaceutically acceptable excipient, selected from lubricants, preferably magnesium stearate.

33. Embodiment

Sucroferric oxyhydroxide particles comprising sucroferric oxyhydroxide and optionally at least one further pharmaceutically acceptable excipient, wherein:
xxiv) at least 40%, or at least 60%, or at least 80%, or at least 90% of the sucroferric oxyhydroxide particles in the particle size distribution are between 4 to 200 µm or between 5 to 160 µm or between 21 to 160 µm,
xxv) the sucroferric oxyhydroxide particles have a d50 in the particle size distribution of between 30 µm to 120 µm, or 35 µm to 110 µm, or 40 µm to 100 µm, or preferably between 40 µm to 80 µm.

34. Embodiment

A tablet, a pharmaceutical formulation, a pharmaceutical composition or a use, according to any of the previous embodiments, wherein the sucroferric oxyhydroxide represents more than 80% or more than 90%, or more than 95% of the sucroferric oxyhydroxide particles, by weight on a dry weight basis of the particles.

35. Embodiment

Use of a pharmaceutical composition according to any of the previous embodiments, still in the form of a powder, for the manufacture a compressed tablet.

36. Embodiment

A tablet, a pharmaceutical composition or a use, according to any of the previous embodiments, wherein at least 50%, or at least 60% of the sucroferric oxyhydroxide particles in the particle size distribution, have a particle size the range of 30 to 200 μm or preferably between 40 to 200 μm.

37. Embodiment

A tablet, a pharmaceutical composition or a use according to any of the previous embodiments, wherein the embodiment refers to a dry form of the tablet or of the pharmaceutical composition.

38. Embodiment

A tablet or a pharmaceutical composition according to any of the previous embodiments, wherein the sucroferric oxyhydroxide particles have a particle size distribution curve as depicted in FIG. 2.

39. Embodiment

A tablet or a pharmaceutical composition according to any of the previous embodiments, wherein the sucroferric oxyhydroxide particles have a particle size distribution curve in which the peak of the curve is between 50 μm and 90 μm.

The invention claimed is:

1. A pharmaceutical composition for oral administration comprising sucroferric oxyhydroxide;
   wherein the pharmaceutical composition is in the form of a chewable tablet;
   wherein the chewable tablet has a disintegration time of between 5 minutes and 18 minutes as measured according to the European Pharmacopoeia 04/2011:20901;
   wherein the hardness of the chewable tablet is between 100 N to 200 N as measured according to the European Pharmacopoeia 01/2008:20908;
   wherein the weight of the chewable tablet is between 2000 mg and 3000 mg;
   wherein more than 65% of the weight of the chewable tablet (by weight on a dry weight basis) is sucroferric oxyhydroxide; and
   wherein the chewable tablet is prepared using sucroferric oxyhydroxide particles, wherein at least 80% by volume of the sucroferric oxyhydroxide particles have a particle size in the range of 4 μm to 200 μm and the d50 particle size distribution by volume of the sucroferric oxyhydroxide particles is in the range of 30 μm to 80 μm.

2. The pharmaceutical composition according to claim 1, wherein at least 80% by volume of the sucroferric oxyhydroxide particles have a particle size in the range of 5 μm to 160 μm.

3. The pharmaceutical composition according to claim 1, wherein at least 90% by volume of the sucroferric oxyhydroxide particles have a particle size in the range of 4 μm to 200 μm.

4. The pharmaceutical composition according to claim 1, wherein the friability of the chewable tablet is between 0% to 7% as measured according to the European Pharmacopoeia 01/2010:20907.

5. The pharmaceutical composition according to claim 1, wherein the chewable tablet is formed by direct compression.

6. A pharmaceutical composition for oral administration comprising about 2500 mg of sucroferric oxyhydroxide;
   wherein the pharmaceutical composition is in the form of a chewable tablet;
   wherein the chewable tablet has a disintegration time of between 5 minutes and 18 minutes as measured according to the European Pharmacopoeia 04/2011:20901;
   wherein the hardness of the chewable tablet is between 100 N to 200 N as measured according to the European Pharmacopoeia 01/2008:20908;
   wherein more than 65% of the weight of the chewable tablet (by weight on a dry weight basis) is sucroferric oxyhydroxide; and
   wherein the chewable tablet is prepared using sucroferric oxyhydroxide particles, wherein at least 80% by volume of the sucroferric oxyhydroxide particles have a particle size in the range of 4 μm to 200 μm and the d50 particle size distribution by volume of the sucroferric oxyhydroxide particles is in the range of 30 μm to 80 μm.

7. The pharmaceutical composition according to claim 6, wherein at least 80% by volume of the sucroferric oxyhydroxide particles have a particle size in the range of 5 μm to 160 μm.

8. The pharmaceutical composition according to claim 6, wherein the chewable tablet is a compressed tablet.

9. The pharmaceutical composition according to claim 6, wherein the chewable tablet is formed by direct compression.

10. The pharmaceutical composition according to claim 6, wherein the friability of the tablet is between 0% to 7% as measured according to the European Pharmacopoeia 01/2010:20907.

11. A pharmaceutical composition for oral administration comprising sucroferric oxyhydroxide;
    wherein the pharmaceutical composition is in the form of a chewable tablet;
    wherein the weight of the chewable tablet is between 2000 mg and 3000 mg;
    wherein the chewable tablet has a disintegration time of between 5 minutes and 18 minutes as measured according to the European Pharmacopoeia 04/2011:20901;
    wherein the hardness of the chewable tablet is between 100 N to 200 N as measured according to the European Pharmacopoeia 01/2008:20908;
    wherein more than 80% of the weight of the chewable tablet (by weight on a dry weight basis) is sucroferric oxyhydroxide; and
    wherein the chewable tablet is prepared using sucroferric oxyhydroxide particles, wherein at least 80% by volume of the sucroferric oxyhydroxide particles have a particle size in the range of 4 μm to 200 μm and the d50 particle size distribution by volume of the sucroferric oxyhydroxide particles is in the range of 30 μm to 80 μm.

12. The pharmaceutical composition according to claim 11, wherein at least 80% by volume of the sucroferric oxyhydroxide particles have a particle size in the range of 5 μm to 160 μm.

13. The pharmaceutical composition according to claim 11, wherein at least 90% by volume of the sucroferric oxyhydroxide particles have a particle size in the range of 5 μm to 160 μm.

14. The pharmaceutical composition according to claim 11, wherein the chewable tablet is a compressed tablet.

15. The pharmaceutical composition according to claim 11, wherein the chewable tablet is formed by direct compression.

16. The pharmaceutical composition according to claim 11, wherein the friability of the chewable tablet is between 0% to 7% as measured according to the European Pharmacopoeia 01/2010:20907.

* * * * *